United States Patent [19]

Summerton et al.

[11] Patent Number: 6,030,941
[45] Date of Patent: *Feb. 29, 2000

[54] POLYMER COMPOSITION FOR DELIVERING SUBSTANCES IN LIVING ORGANISMS

[75] Inventors: James E. Summerton; Dwight D. Weller, both of Corvallis, Oreg.

[73] Assignee: AVI BioPharma, Inc., Portland, Oreg.

[*] Notice: This patent issued on a continued prosecution application filed under 37 CFR 1.53(d), and is subject to the twenty year patent term provisions of 35 U.S.C. 154(a)(2).

[21] Appl. No.: 08/848,844

[22] Filed: Apr. 30, 1997

Related U.S. Application Data

[60] Provisional application No. 60/016,347, May 1, 1996, and provisional application No. 60/028,609, Oct. 23, 1996.

[51] Int. Cl.[7] .................................................. A01N 37/18

[52] U.S. Cl. ................................ 514/2; 514/12; 514/772; 514/773; 514/21

[58] Field of Search ................................ 424/401; 514/2, 514/12, 21, 772, 773

[56] References Cited

U.S. PATENT DOCUMENTS

| | | | |
|---|---|---|---|
| 4,356,166 | 10/1982 | Peterson et al. | 424/19 |
| 5,087,616 | 2/1992 | Myers et al. | 514/21 |
| 5,593,974 | 1/1997 | Rosenberg et al. | 514/44 |
| 5,626,862 | 5/1997 | Brem et al. | 424/426 |

FOREIGN PATENT DOCUMENTS

| | | |
|---|---|---|
| 1 541 436 | 2/1979 | United Kingdom . |
| 92/02255 | 2/1992 | WIPO . |
| 92/10212 | 6/1992 | WIPO . |
| 97/33552 | 9/1997 | WIPO . |

OTHER PUBLICATIONS

International Search Report.
Adams, N.W., et al., "Controlled Release Polyamino Acid–drug Conjugates for Subcutaneous Injection," 198th American Chemical Society National Meeting, Miami Beach, Florida, USA, Sep. 10–15, 1989. In: Abstr Pap Am Chem Soc, vol. 198, Abstr No. 113.
Anderson, R.G.W., et al., "Potocytosis: Sequestration and Transport of Small Molecules by Caveolae, " Science 255:410–411 (1992).
Bennett, D.B. et al., "Drug–Coupled Poly(Amino Acids) As Polymeric Prodrugs," J. of Bioactive and Compatible Polymers 3:44–52 (1988).
Fabre, I., et al., "Polyglutamylation, an Important Element in Methoxetrate Cytotoxicity and Selectivity in Tumor Versus Murine Granulocytic Progenitor Cells in Vitro," Cancer Res. 44:3190–3195 (1984).
Kato, Y., et al., "Antitumor Activity of 1–β–D–Arabinofuranosylcytosine Conjugated with Polyglutamic Acid and Its Derivative," Cancer Res. 44:25–30 (1984).
Kim, C–K, et al, "Effects of molecular Weights on the Physio–Pharmaceutical Properties of Poly–L–Glutamic Acid Cytarabine Conjugates," Biol. Abstr. vol.BA88 Abstr. No. 110606.
Li, C., et al., "Development of a Highly Efficacious Water–Soluble Polymer–Taxol Conjugate," Proc. of the Eigthy–Eighth Annual Meeting of the American Association for Cancer Res., San Diego, California, USA, Apr. 12–16, 1997, #1731 pp. 258.

(List continued on next page.)

Primary Examiner—Thurman K. Page
Assistant Examiner—L. Channavajjala
Attorney, Agent, or Firm—LeeAnn Gorthey; Dehlinger & Associates

[57] ABSTRACT

Polymeric compositions effective for delivering compounds in living organisms are described. The compositions include polypeptides which exhibit solubility in both hydrophilic and lipophilic environments by undergoing a reversible pH-dependent transition from a low-pH, lipophilic form to a high-pH, hydrophilic form.

20 Claims, 22 Drawing Sheets

OTHER PUBLICATIONS

Malley, A., and L. Deppe, "Anti–Timothy IgE Formation: Supression with Antigen D–dGI Conjugates," Int. Archs Allergy appl. Immun. 63:113–120 (1980).

McCormick–Thompson, L. and R. Duncan, "Poly(amino acid) Copolymers as a PotentialSoluble Drug Delivery System. 1. Pinocytic Uptake and Lysosomal Degradation Measured In Vitro," J. of Bioacitve and Compatible Polymers 4:242–250 (1989).

McCormick–Thompson, L., et al., "Poly(amino acid) Copolymers as a Potential Soluble Drug Delivery System. 2. Body Distribution and Preliminary Biocompatibility Testing In Vitro and in Vivo," J. of Bioactive and Compatible Polymers 4:252–268 (1989).

Morimoto, Y., et al., "Antitumor Agent Poly (Amino Acid) Conjugates as a Drug Carrier in Cancer Chemotherapy," J. Pharm. Dyn. 7:688–698 (1984).

Rosenablatt, D. and V.M. Whitehead, "Methotrexate Polyglutamates in Cultured Human Cells," Adv. Exp. Med. Biol. 163 :275–285 (1983).

Rosenblatt, D.S., et al., "Differential Effects of Folinic Acid and Glycine, Adenosine, and Thymidine as Rescue Agents in Methotrexate–Treated Human Cells in Relation to the Accumulation of Methotrexate Polyglutamates," Molecular Pharmacology 21:718–722 (1982).

Tannock, I., and D. Rotin, "Acids pH in Tumors and Its Potential for Therapeutic Exploitation," Cancer Res. 49:4373–4384 (1989).

Vaupel, P. et al., "Blood Flow, Oxygen and Nutrient Supply, and Metabolic Microenvironment of Human Tumors: A Review," Cancer Res. 49:6449–6465 (1989).

Hoes, C.J.T. et al., "Development of Macromolecular Prodrugs of the Antitumor Antibiotic Adriamycin," *Makromol. Chem. Suppl.* 9:175–178 (1985).

Hoes, C.J.T. et al., "Biological Properties of Adriamycin Bound to Biodegradable Polymeric Carriers," *J. Controlled Rel.* 23:37–54 (1993).

Nukui, M. et al., "Association of Macromolecular Prodrugs Consisting of Adriamycin Bound to Poly(L–glutamic acid)," *Makromol. Chem.* 192:2925–2942 (1991).

Takizawa, A., et al., "Solubilities of Polypeptides with Hydrophobic and Negatively Charnged Side–Chains into Cationic Artificial Membrane Vesicles," *Colloid & Polymer Sci.* 265:31–36 (1987).

Anderson, D.C. et al., "Enhanced In Vitro Tumor cell Retention and Internalization of Antibody Derivatized with Synthetic Peptides," *Bioconjugate Chem.* 4:10–18 (1993).

Bongartz, J.–P. et al., "Improved Biological Activity of Antisense Oligonucleotides Conjugated to a Fusogenic Peptide," *Nuc. Acids Res.* 22(22) :4681–4688 (1994).

Fattal, E. et al., "Pore–Forming Peptides Induce Rapid Phospholipid Flip–Flop in Membranes," *Biochemistry* 33:6721–6731 (1994).

Haensler, J., and Szoka, F.C., Jr., "Polyamidoamine Cascade Polymers Mediate Efficient Transfection of Cells in Culture," *Bioconjugate Chem.* 4:372–379 (1993).

Parente, R.A. et al., "Association of a pH–Sensitive Peptide with Membrane Vesicles: Role of Amino Acid Sequence," *Biochemistry* 29:8713–8719 (1990a).

Parente, R.A. et al., "Mechanism of Leakage of Phospholipid Vesicle Contents Induced by the Peptide GALA," *Biochemistry* 29:8720–8728 (1990b).

Plank, C. et al., "The Influence of Endosome–Disruptive Peptides on Gene Transfer Using Synthetic Virus–Like Gene Transfer Systems," *J. Biol. Chem.* 269(17):12918–12924 (1994).

Subbarao, N.K. et al., "pH–Dependent Bilayer Destabilization by an Amphipathic Peptide," *Biochemistry* 26:2965–2972 (1987).

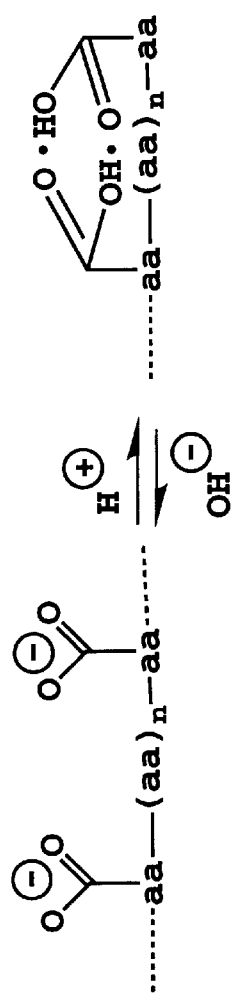
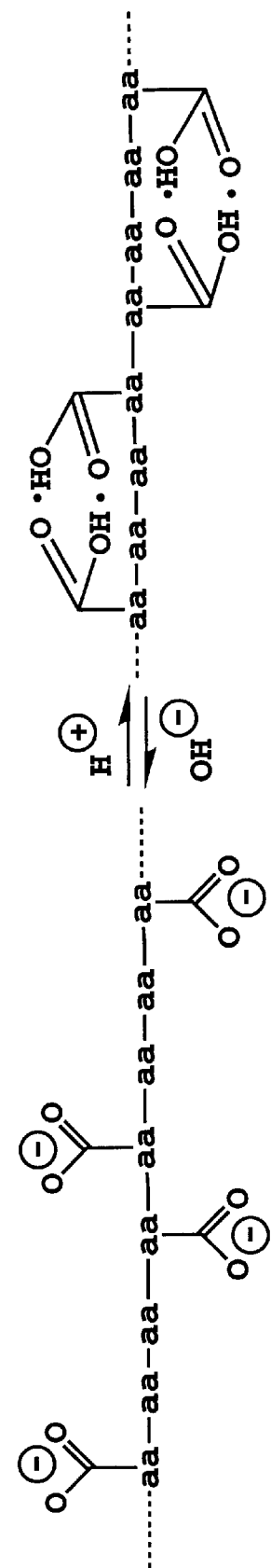
Fig 1A
Fig 1B

Fig. 7B
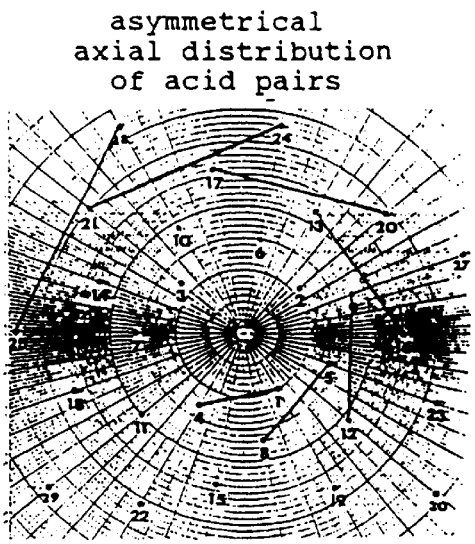
asymmetrical axial distribution of acid pairs
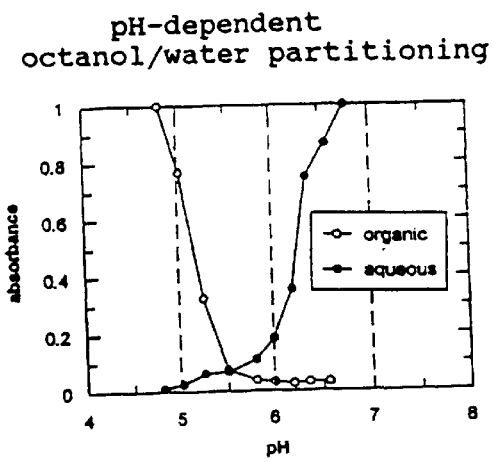
pH-dependent octanol/water partitioning
Polypeptide sequence: ELLDELLDELLDELLDELLDELLß
D = aspartic acid
E = glutamic acid
L = leucine
ß = ß-alanine
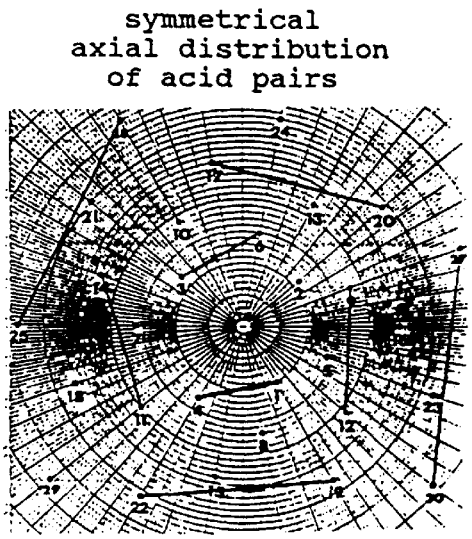
symmetrical axial distribution of acid pairs
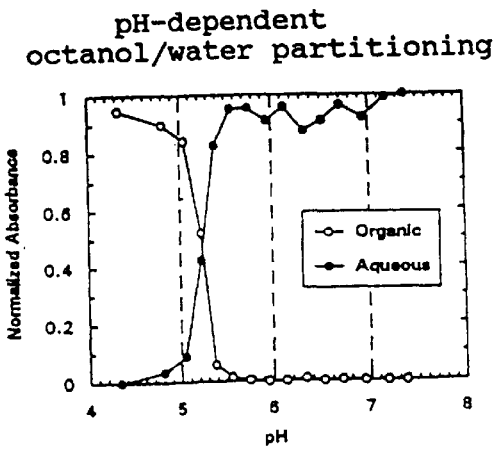
pH-dependent octanol/water partitioning
Polypeptide sequence: ELEDLDLLELEDLDLLELEDLDLLELEDLß
Fig. 7C

POLYMER COMPOSITION FOR DELIVERING SUBSTANCES IN LIVING ORGANISMS

This application claims the priority of U.S. Provisional Application Ser. Nos. 60/016,347, filed May 1, 1996, and 60/028,609, filed Oct. 23, 1996, both pending, which are incorporated herein by reference.

FIELD OF THE INVENTION

The invention relates to the use of polymeric compositions effective for delivering compounds in living organisms. The compositions exhibit solubility in both hydrophilic and lipophilic environments by undergoing a reversible pH-dependent transition from a low-pH, lipophilic form to a high-pH, hydrophilic form.

REFERENCES

Anderson, R. G. W. et al., *Science* 255:410–411 (1992).

Atherton, Cameron, and Sheppard, *Tetrahedron* 44:843 (1988).

Aungst et al., *Int. J. Pharmaceut.* 33:225 (1986).

Blout, E. R. et al., *J. Am. Chem. Soc.* 78:497

Chen and Tai, *Res. Comm. Molec. Path. & Pharm.* 88:317 (1995).

Chopra, I., *Parasitology* 96:25–44 (1988).

Clague, M. J. et al., *J. Biol. Chem.* 269:21–24 (1994).

Dawson et al., *Science* 226:776 (1994).

Deshpande, D. et al., *Pharm. Res.* 13(1):57–61 (1996).

Dixon, J. S., *Scand. J. Gastroenterol. Suppl.* 212:48–62 (1995).

Doty et al., *J. Polymer Sci.* 23:851 (1957).

Eberle and Nuninger, *J. Org. Chem.* 57:2689 (1992).

Fuchs, R. et al., *J. Biol. Chem.* 264:2212–2220 (1989).

Glupczynski, Y. et al., *Am J. Gastroentrol.* 85:1545–51 (1990).

Golden et al., *J. Invest. Dermatol.* 86 255 (1986).

Goodman and Barry, *J. Pharm. Pharmacol.* 37:80P (1985).

Goodman and Barry, *J. Pharm. Pharmacol.* 38:71P (1986).

Gueritte-Vogelein et al., *J. Med. Chem.* 34:992 (1991).

Hanabusa et al., *J. Polym. Sci. Polym. Lett. Ed.* 22:559–564 (1984).

Hoes et al., *Makromol. Chem. Suppl.* 9:175 (1985).

Igarishi, K. et al., *Caries Res.* 24(1):52–58 (1990).

Kametani et al, *Chem Pharm Bull.* 30:4545 (1982).

Kennedy, K. A. et al., *Biochem. Pharm.* 29:1–8 (1980).

Korting, H. C. et al., *Clin. Investig.* 71(8):644–648 (1993).

Leo, Hansch, and Elkins, *Chemical Reviews* 71:525 (1971).

Ludwig, LeBorgue, and Hoflack, *Trends in Cell Biol.* 5:202 (1995).

Mathew et al., *J. Med. Chem.* 35:145–151 (1992).

Mathias, C. J. et al., *J. Nucl. Med.* 37(6):1003–1008 (1996).

Nukui et al., *Makromol. Chem* 192:2925 (1991).

O'Connor, H. J., *Eur. J. Gastroenterol. Hepatol.* 6 (Suppl. 1) :113–9 (1994).

Rapaport, E. et al., *Proc. Natl. Acad. Sci USA,* 93(2) :709–713 (1996).

Rehfeld and Elias, *J. Invest. Dermatol.* 79:1 (1982).

Summerton, J. E. and Weller, D. D., U.S. Pat. No. 5,185,444 (1993).

Tannock, I. F. et al., *Cancer Res.* 49:4373–4384 (1989).

Vaupel, P. et al., *Cancer Res.* 49:6449–6465 (1989).

van Houte, J. et al., *J. Dent. Res.* 75(4):1008–1014 (1996).

Yosipovitch, G. et al., *Nephrol. Dial. Transplant.* 8(10): 1129–1132 (1993).

BACKGROUND OF THE INVENTION

Lipid layers, such as comprise cell membranes and the extracellular matrix of the stratum corneum, can constitute a formidable barrier to drug delivery. For optimal delivery, a drug should freely dissolve in both the aqueous compartments of the body and the lipid layers which enclose those compartments.

Although many low-molecular-weight compounds of low to moderate polarity can pass directly through lipid layers, compounds with greater polarity and/or higher molecular weight generally enter eukaryotic cells only via endocytosis or related processes. In this process, compounds are taken into the cell via progressive invagination of a region of the membrane, eventually forming a closed vesicle, or endosome, within the cell. In most cases, the endosome then merges with a lysosome, resulting in exposure of the internalized compound to degradative enzymes.

To facilitate more effective delivery of drugs and other compounds across lipid layers, it would be desirable to provide a drug transporting composition which affords lipid solubility under selected conditions and aqueous solubility under other conditions. It would also be desirable to deliver compounds into the cell cytosol via a route which avoids exposure to lysosomal enzymes.

SUMMARY OF THE INVENTION

In one aspect, the invention provides a composition for transporting a compound from a low-pH environment across a lipid layer to a higher-pH aqueous compartment. The composition includes a polypeptide having one or more pairs of carboxyl groups, where the carboxyl groups of a pair are separated by zero, two or three amino acids, and a length of between about 8 and about 100 amino acid residues, and preferably between 10 and 50 residues. The polypeptide further contains an initiator moiety at one end region of the polypeptide, to facilitate entry of said end region, and partitioning of the polypeptide, into the lipid layer. Such a polypeptide is effective to undergo a reversible transition between a lipophilic form, which is effective to partition from the low-pH environment into the lipid layer, and a hydrophilic form, which is effective to partition preferentially from the lipid layer into the higher-pH aqueous compartment. The polypeptide is thereby able to traverse the lipid layer from the low-pH environment to the higher-pH compartment. The composition also includes, covalently attached to the polypeptide, the compound to be transported.

In one preferred embodiment, 30–100 percent of the amino acid residues forming the polypeptide, excluding the initiator moiety, are glutamic acid. Pairs of glutamic acid residues in the polypeptide may be separated by other amino acid residues, which are preferably selected from the group consisting of leucine, methionine, alanine, and 2-amino butyric acid. Alternatively, the polypeptide may be polyglutamic acid having an initiator moiety at one end region.

The initiator moiety may be an initiator amino acid sequence having 3–12 amino acid residues. The sequence is effective to form an alpha helix at a pH higher than the pH at which a same-length polyglutamic acid forms an alpha helix. Preferred amino acid residues in such a sequence are glutamic acid, leucine, methionine, alanine, 2-aminobutyric acid, norvaline, and β-alanine, where the ratio of non-glutamic acid to glutamic acid residues is greater than 1. Where the polypeptide component contains a sequence having less than about 50% glutamic acid residues, the initiator sequence may be an end region of the polypeptide itself.

Alternatively, there may be a group linked covalently to the N or C terminus which is effective to eliminate a positive or negative charge at said terminus, and which has at least one remote polar group effective to shield polar sites near the terminus. A lipophilic substance at the terminus, including a compound to be delivered, may serve as an initiator moiety. A single polypeptide may also contain a combination of such initiator moieties.

The compound to be delivered may be attached to an end of the polypeptide component, typically the end opposite the initiator sequence. The composition may have only one, or multiple compounds per polypeptide component. The compound to be delivered may include a compound which is itself only sparingly soluble in free form in an injectable aqueous delivery medium, such as taxol, cyclosporin, amphotericin B. In another embodiment, the compound is a sequence-specific nucleic acid binding polymer, e.g., an antisense compound.

In another aspect, the invention provides a method of facilitating the transport of a compound from a low-pH environment across a lipid layer to a higher-pH aqueous compartment. According to the method, the compound is covalently coupled to a polypeptide as described above. The method is useful, for example, in delivering a therapeutic compound from an extracellular medium, having a given pH, to the cytosol of a cell, having a higher pH. In one specific application, the method is used in antitumor therapy, where the cell is a tumor cell existing in an acidic extracellular medium, and the attached compound is an antineoplastic agent. In other applications, the method is used in the treatment of *H. pylori* infection, where the extracellular medium is stomach fluid, the cell is an *H. pylori* bacterial cell, and the compound is an antibacterial agent, or in the treatment and prevention of tooth decay, where the cell is an acid-producing cariogenic bacterial cell, and the attached compound is an agent effective against cariogenic bacteria.

Further applications include transdermal delivery of a compound through the stratum corneum, wherein the lipid layer to be traversed comprises the extracellular matrix of the stratum corneum, and in transporting a compound across the brain-blood barrier. In the latter case, the composition is transported within a transcytotic vesicle through an endothelial cell of a capillary wall, and is taken up by a brain cell within an endocytotic vesicle.

These and other and features of the invention will become more fully apparent when the following detailed description of the invention is read in conjunction with the accompanying drawings.

BRIEF DESCRIPTION OF THE DRAWINGS

FIGS. 1A–1B illustrate a pH-dependent transition between hydrophilic and lipophilic conformations of side chain carboxyls of a polymer;

FIGS. 7B and 7C show a comparison of polymers with differing axial distributions of paired carboxyls;

FIG. 8A shows a polyglutamic acid with unmodified termini, FIG. 8B illustrates the incorporation of groups which delete or shield polar sites, and FIG. 8C shows further addition of lipophilic amino acid residues at the termini;

DETAILED DESCRIPTION OF THE INVENTION

I. Definitions

Figure 2A:
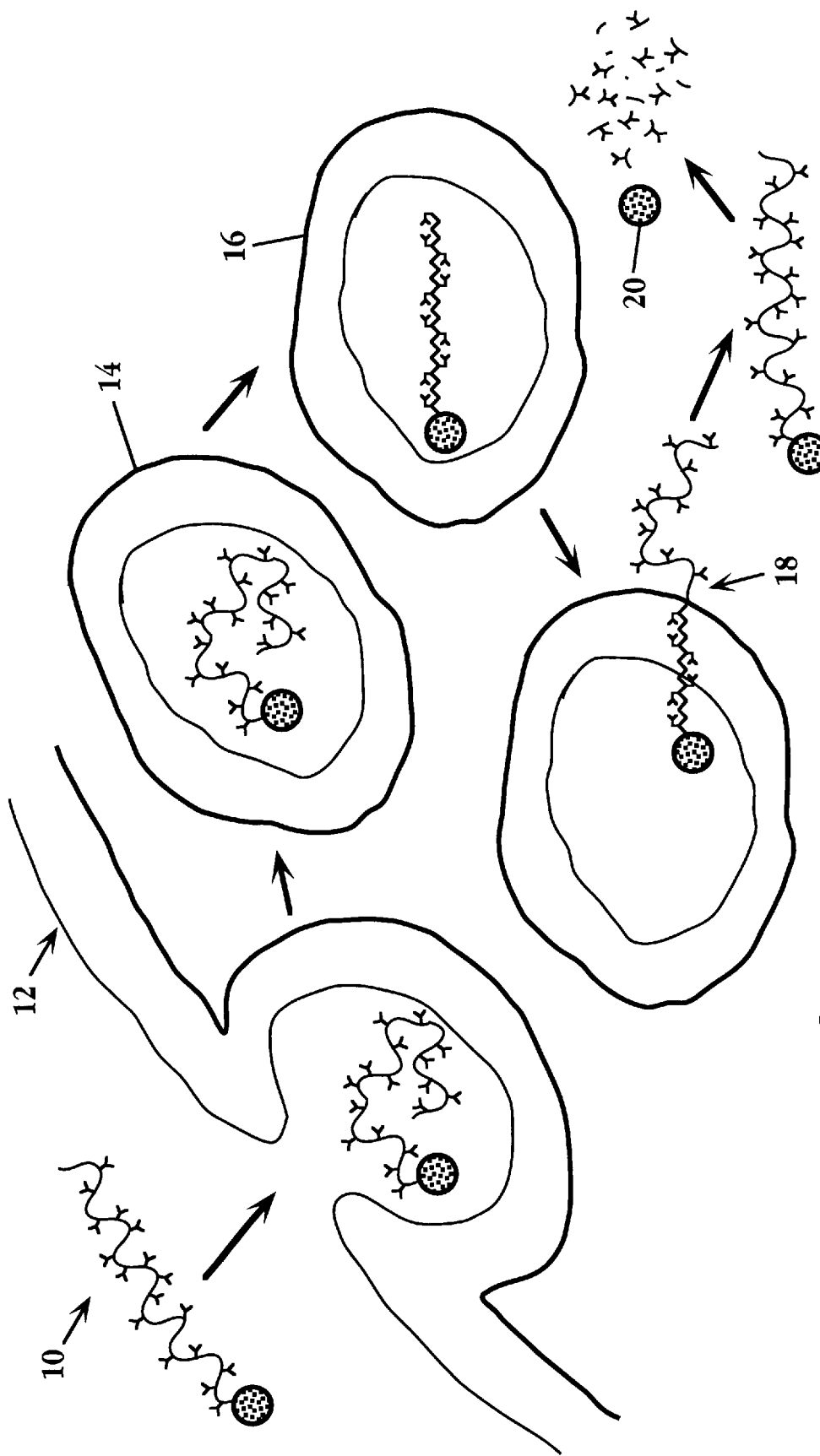
FIG. 2A depicts the process of cytosolic entry, via endocytosis, of a polypeptide with attached compound, in accordance with one aspect of the invention.

The terms below have the following meanings unless otherwise noted.

The "low pH form" (also low pH conformation, lipophilic form, or lipophilic conformation) of a polypeptide of the invention, or a segment of the polypeptide, is a substantially non-ionic a-helical conformation rendered lipophilic by hydrogen bonding between paired side-chain or terminal carboxyl groups.

The "high pH form" (also high pH conformation, hydrophilic form, or hydrophilic conformation) of a polypeptide of the invention, or a segment of the polypeptide, is a conformation in which the side-chain or terminal carboxyl groups are wholly or predominantly in a non-hydrogen-bonded, ionic state.

A "reversible transition" between the lipophilic form and the hydrophilic form of a polypeptide is a transition between a nonionic, α-helical conformation, wherein side chain carboxyls are engaged in intramolecular hydrogen bonding, favored by low pH, and a form wherein side chain carboxyls are in ionic, non-hydrogen-bonded states, favored by high pH. Such a transition may encompass an entire polypeptide, or it may occur at a localized region of a polypeptide, particularly when the region is in the vicinity of an aqueous/lipid interface, or has a composition that is especially lipophilic and/or especially favors the formation of an α-helix. Such a localized region of a polypeptide is often effective to initiate entry of the polypeptide into a lipid phase, such as a membrane, even though regions of the polypeptide more remote from the lipid phase may be in a hydrophilic conformation.

An "acid amino acid" or "acid side chain acid" is one which has a free carboxyl group when incorporated into a polypeptide. Examples are aspartic acid and glutamic acid.

A "non-acid amino acid" or "non acid side chain acid" is one which has no free carboxyl group when incorporated into a polypeptide.

A "high glutamic" polypeptide is a polypeptide containing greater than about 50% glutamic acid residues.

An "initiator sequence" is a short (typically 3–12 amino acid residues) sequence at a terminus of a polypeptide which readily forms an α-helix at pH's attainable in endosomes of mammalian cells, generally at a pH significantly higher than that at which the same length sequence of glutamic acid residues would form an α-helix. Such a sequence at the terminus of a polypeptide initiates entry of the polypeptide into a lipid layer and promotes α-helix formation in immediately adjacent segments of the polypeptide.

A group which "deletes" or "shields" polar groups at or near the terminus of a polypeptide is a covalently linked moiety which caps or replaces a carboxylate anion or protonated amine at the terminus. Preferred groups further mask other polar sites near the terminus by non-covalent associations, typically hydrogen bonding.

"Endocytosis" is a process by which extracellular material is taken into a cell via an invagination of the cell membrane, which closes to form a vesicle within the cell known as an endosome. Endocytosis may be receptor-mediated, where the extracellular compound binds to a specific receptor on the cell surface, or extracellular compounds may be imported nonspecifically, by virtue of their presence near the cell membrane. The latter process is also known as fluid-phase endocytosis or pinocytosis. A related process, potocytosis, takes compounds into the cell via vesicles near the cell surface known as caveolae. In all of the above processes, the vesicles enclosing the extracellular compound become increasingly acidic after formation. The compositions and methods of the invention are therefore applicable to all of these methods of transport.

II. Polymer Composition

The polymer composition of the invention includes a polypeptide component capable of undergoing a transition between a hydrophobic, α-helical form, and a hydrophilic form; an initiator moiety at one end region of the polypeptide, to facilitate partitioning of the polypeptide into a lipid layer through that end region, and the compound to be delivered, covalently attached to the polypeptide.

As detailed below, the polypeptide component contains one or more pairs, and preferably two or more pairs, of carboxyl groups, where the two carboxyls of a pair are separated by zero, two or three amino acids. The composition and positioning of the amino acids of the polypeptide are such that, in the presence of both an aqueous and a lipid-like phase, the polypeptide undergoes, typically at a pH between about 4.0 and about 7.0, a reversible transition between a high-pH form, comprising a multiply-ionized hydrophilic structure, and a low-pH form, comprising a substantially non-ionic a-helical structure rendered lipophilic by hydrogen bonding between the paired carboxyls.

The lipophilic, low-pH form partitions into a lipid environment, while the hydrophilic, high-pH form partitions preferentially into aqueous solution. FIG. 1A illustrates the pH-dependent transition between hydrophilic and lipophilic forms of a polypeptide, and FIG. 1B illustrates this solubility transition for a specific sequence of properly-spaced carboxyl-containing amino acid pairs.

A. Composition Transport Across a Lipid Layer

The polymer composition can be used to transport an attached compound from the extracellular compartment to the cytosolic compartment within cells. The process is illustrated in FIG. 2A. The composition 10 is readily delivered, in an aqueous vehicle, to the extracellular compartment by virtue of the aqueous solubility imparted by the high-pH form of the polypeptide. Following endocytosis by a cell 12, the composition is enclosed within an endosome 14. The pH within the endosome decreases due to the action of ATP-driven proton pumps within the endosomal membrane (see e.g. Clague, Fuchs). The composition converts, in the increasingly acidic environment of the late stage endosome, shown at 16, to its low-pH lipid-soluble form, which enters the endosomal membrane.

Figure 2B:
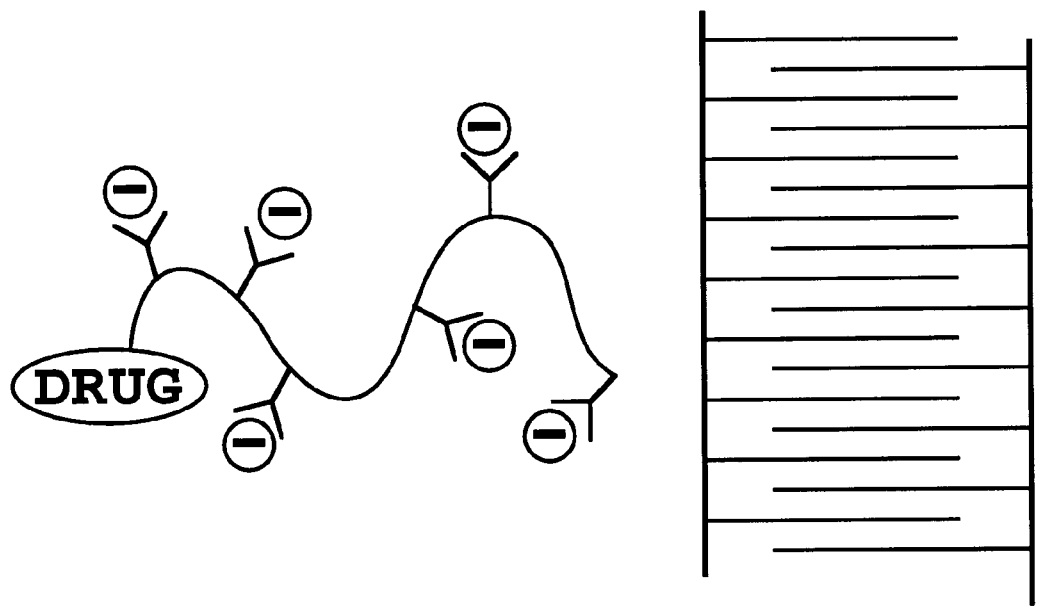
FIG. 2B shows the polypeptide-compound complex in its high pH form, which exists in the early-stage endosome.
Figure 2C:
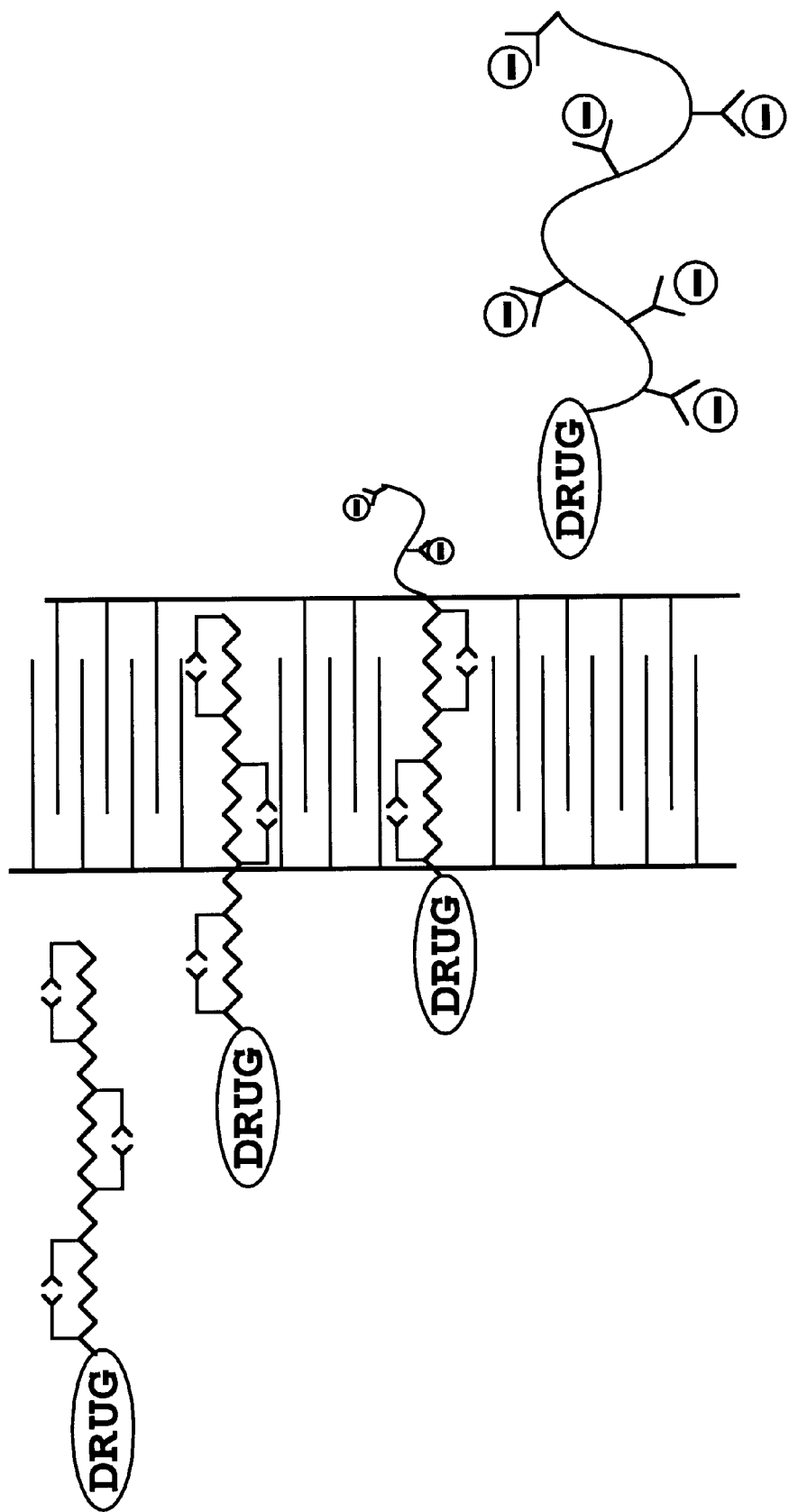
FIG. 2C shows the complex in its low pH form, which exists in the late-stage endosome, entering the lipid membrane, and converting back to the high pH form upon contacting the higher pH cytosol.

Upon contacting the cytosolic face of the endosomal membrane, the composition is actively drawn into the cytosol by virtue of progressive ionization and solvation of the polypeptide chain at the near-neutral pH of the aqueous cytosol, as shown at 18, resulting in delivery of the attached compound 20 into the desired subcellular compartment. As discussed further below, a polypeptide constructed from L-amino acids will typically be degraded in the cytosol, as shown, after the drug has been released. This unidirectional active transport process is illustrated further in FIGS. 2B and 2C, where only a portion of the endosomal membrane is represented.

The above figures depict the polypeptide assuming a completely hydrogen-bonded conformation prior to entering the endosomal membrane. Such is likely to occur when the polypeptide is of a composition that readily forms an α-helix at relatively high pH. However, for highly polar peptides, i.e. those containing a high percentage of acid side chain residues, entry into the membrane may be initiated by a localized lipophilic region of the polypeptide, even when other regions of the polypeptide are in a non-hydrogen-bonded, hydrophilic conformation. Such entry is especially favored when this lipophilic region is at a terminus of the polypeptide. Accordingly, a terminus of the polypeptide, especially a longer polypeptide containing a high concentration of polar groups, may comprise amino acid sequences which readily assume a lipophilic conformation at a relatively high pH, or may be otherwise modified to render the terminus more lipophilic. Such modifications are discussed further below.

An advantage of the composition of the invention, as can be seen from the above description, is that endosome-to-cytosol transport may be achieved without disruption of the endosomal membrane, thus avoiding leakage of lysosomal enzymes into the cytosolic compartment of the cell.

The polymer composition can also be used to transport an attached compound directly into the cytosol of cells in cases where the extracellular medium has a pH less than the pH of the cytosol of the cells, as described below. This allows, for example, selective delivery of compounds into eukaryotic cells, bacteria or other target cells in acidic environments.

Figure 3:
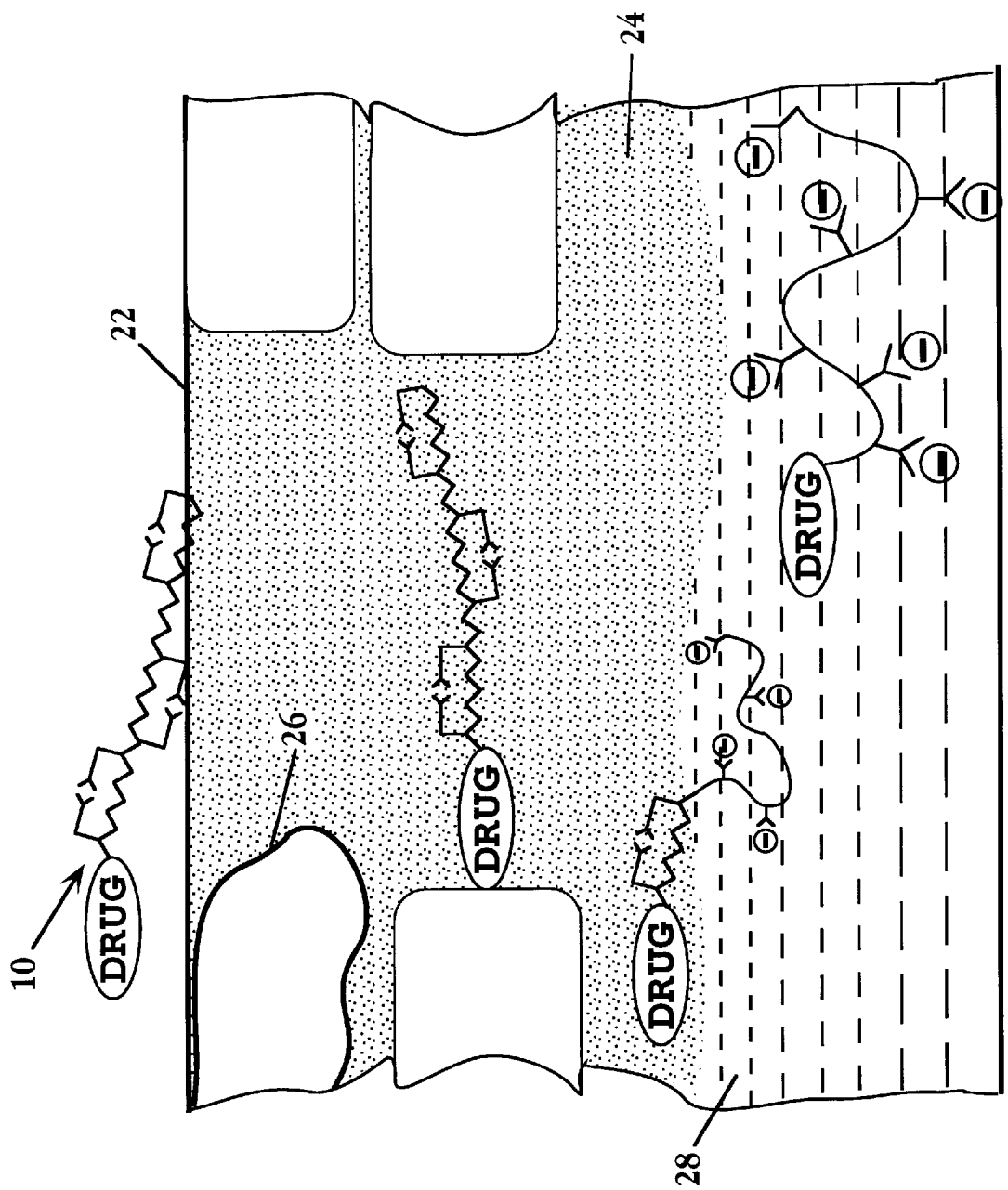
FIG. 3 depicts the transdermal transport process of a polypeptide containing an attached compound, where the complex passes from the extracellular lipid matrix to the aqueous compartment beneath the stratum corneum.

The polymer composition can further be used for transdermal delivery of selected compounds, as described below, and as illustrated in FIG. 3. In this case, the composition 10 is contacted, in its low-pH lipid-soluble form, with the surface of the epidermis, shown at 22, leading to diffusion through the extracellular lipid matrix 24 of the stratum corneum, which contains epithelial cells 26. Upon contact with the aqueous compartment underlying the stratum corneum, shown at 28, the composition is actively drawn into this compartment by virtue of progressive ionization and salvation of the polypeptide chain at the near-neutral pH of this compartment, thereby effecting delivery of the attached compound into the underlying tissues, with subsequent distribution throughout the body.

The compositions are particularly useful for the delivery of compounds which are only sparingly soluble in free form in aqueous delivery media. These compounds include, but are not limited to, Taxol™, Taxol™ analogs, cyclosporin analogs, and amphotericin B. Also contemplated is delivery of sequence-specific nucleic acid binding polymers.

B. Polypeptide Component

Two important structural features of the polypeptide component are that: a) it contains at least one properly-spaced acid pair, and b) it contains a number of amino acids sufficient to adopt a lipophilic α-helix at low pH. In selecting a preferred polymer for a given application, various factors are considered, such as the properties of the compound to be delivered, the compartments from and into which the compound is to be delivered, and the desirability of including end modifications to shield exposed polar sites and increase lipophilicity at the helix termini.

B1. Acidic Amino Acids. To provide the free carboxyl groups which are able to inter-hydrogen bond when the polypeptide is in an α-helical conformation, carboxyl side chain amino acids, preferably aspartic acid and glutamic acid, are included. The preferred number and frequency of these acids is discussed below.

Figure 5C:
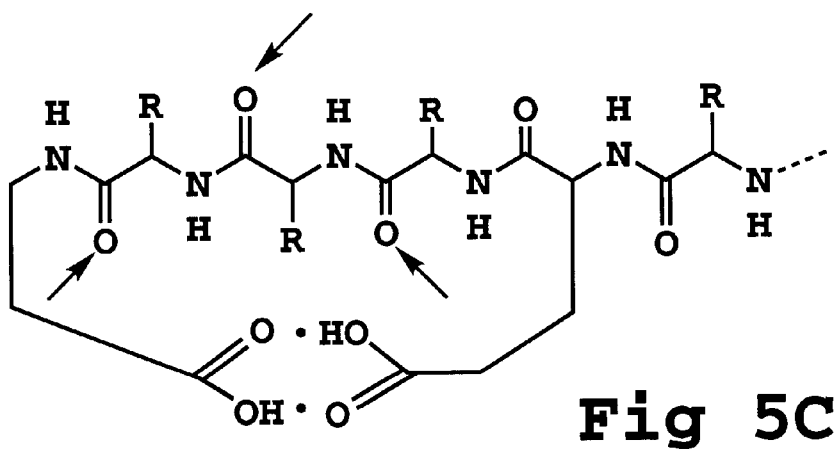
Figure 6A:
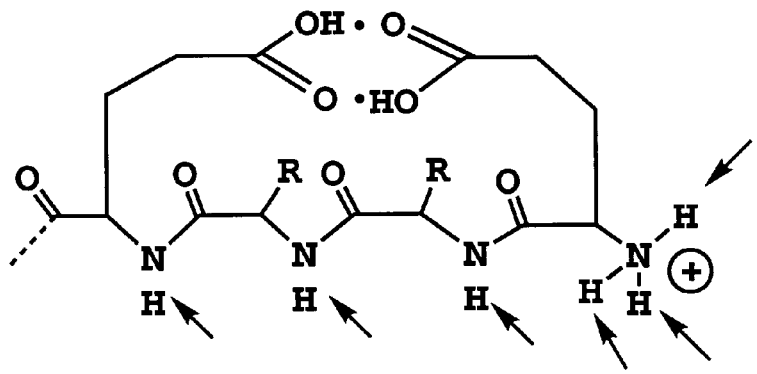
FIGS. 6A–6D shows representative N-terminal end structures of polypeptides, where the structures in 6B–6D have shielded terminal polar sites.
Figure 6B:
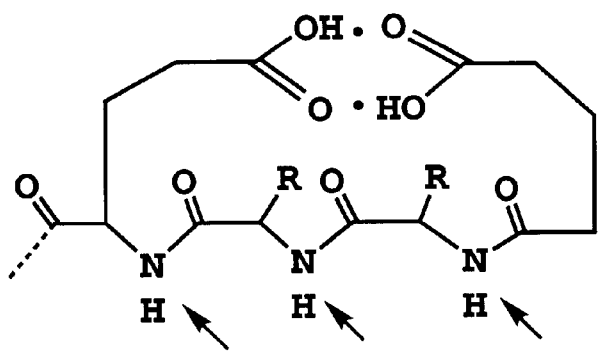

It will be appreciated that a free carboxyl group at either polypeptide terminus may also hydrogen bond with a properly situated carboxyl side chain amino acid. For example, the carboxyl terminus may be prepared with β-alanine, γ-amino butyric acid, or another omega-amino carboxylic acid as its terminal group, by initiating the synthesis of the polypeptide using such an acid, as described in Example 1. This results in an omega-carboxy alkyl amide at the C-terminus (as shown, for example, in FIGS. 10 and 5C), where the carboxyl group at the end of the alkyl chain is available for hydrogen bonding. The N-terminus may be capped with a diacid, such as glutaric acid (as shown in FIG. 6B) to provide an additional hydrogen-bonding carboxyl group.

B2. Non-acidic amino acids. The non-acid amino acids of the polymer, when present, serve principally to provide proper spacing between the two carboxyl groups of each hydrogen-bonding pair, and to adjust the pH of the partitioning transition to a selected value, as discussed below. These amino acids should not contain moieties which are cationic when the polymer is in its low-pH a-helical conformation (i.e., arginine, lysine, and histidine). (An exception is the use of low levels of amino acids such as lysine as sites for attachment of the transported compound, as described in below.) Most of the non-acid amino acids of the polymer are relatively non-polar and compatible with α-helix formation. Accordingly, preferred non-acid amino acids for most applications are selected from the following: tryptophan, phenylalanine, leucine, isoleucine, methionine, valine, and alanine. Norvaline, α-amino butyric acid, and side chain esters of aspartic and glutamic acid are also suitable as "non-acid" amino acids. Based on cost, ease of use, and other practical considerations, leucine, methionine, alanine and α-amino butyric acid are particularly preferred.

With the exception of nucleic acids, polymers with a high density of acid moieties are not natural components of the interior of cells and so could prove toxic therein. However, such toxicity is much reduced or prevented if, after carrying out its drug transport function, said polymers are disassembled into natural subunits endemic in the cytosol of cells. In this regard, it is known that unstructured polypeptides composed of natural L-amino acids can be rapidly depolymerized in the cytosol of cells, primarily in complex multi-ring structures called proteasomes.

For those applications where it is desirable that the polymer be disassembled into innocuous subunits within the cytosol of cells, the preferred amino acids of the polymer are selected from natural L-amino acids. Conversely, for applications where it is desirable that the polymer remain intact in the cytosol, such as those described below, the preferred amino acids are selected from D-amino acids. In the latter applications, other non-natural amino acids are also suitable, such as α-amino butyric acid, norvaline, and norleucine.

Figure 4:
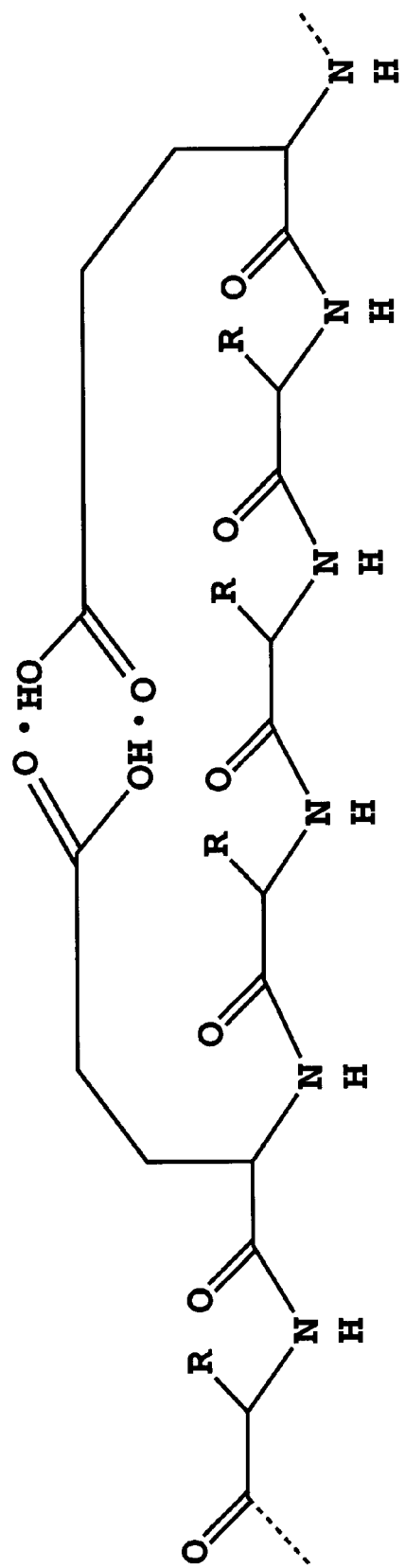
FIG. 4 shows paired, spaced glutamic carboxyls of a polypeptide in an α-helix.

B3. Spacing of Acids. It is known that, in an α-helix conformation, the amide moieties of a polypeptide backbone are effectively shielded from the solvent due to extensive intramolecular hydrogen bonding. It was predicted that, in a polypeptide in an a-helical conformation, proper spacing of acid side chains would substantially shield the polar sites of the acid moieties from the solvent by virtue of formation of double hydrogen bonds between paired acid moieties in their free acid state. Such shielding of the polar sites of the polymer from the environment should result in improved lipid solubility. One such representative structure, comprising paired glutamic acids separated by three amino acids, is shown in FIG. 4.

Studies with CPK molecular models were used to predict the preferred spacing of acid side chains to provide the desired hydrogen-bonded structures. Subsequent octanol/water and pentanol/water partitioning studies with suitable polypeptide sequences verified that good lipid solubility can indeed be achieved at low pH if acid pairs, selected from aspartic and glutamic, are so spaced. Table 1 lists these spacings which provide the desired shielding of polar sites of acid pairs at low pH.

TABLE 1

| |
| --- |
| E-E |
| D-E |
| E-X-X-E |
| E-X-X-D |
| E-X-X-X-E |
| E-X-X-X-D |
| D-X-X-X-E | where:
E = glutamic acid
D = aspartic acid
X = amino acid

As can be seen from the table, spacings of zero, two, or three amino acids between carboxyl side chain amino acids are effective. Of these, spacings of two or three amino acids between carboxyl side chain amino acids are preferred.

Polypeptides containing sequences wherein polar side chains alternate with nonpolar side chains are known to adopt β-sheet and related conformations. Polypeptides with such alternating sequences greater than about 6 amino acids in length were found to be generally insoluble in octanol at low pH, probably due to the formation of multi-chain complexes whose polar sites are not adequately shielded from the solvent. Accordingly, the polymer of the invention should be largely free of significant runs of alternating polar and nonpolar side chains.

B4. Length of Polypeptide. In order to form an α-helix with suitably spaced pairs of carboxyl side chains, the polypeptides of the invention should be at least 8 amino acids in length, and preferably at least 10 amino acids in length.

Figure 7A:
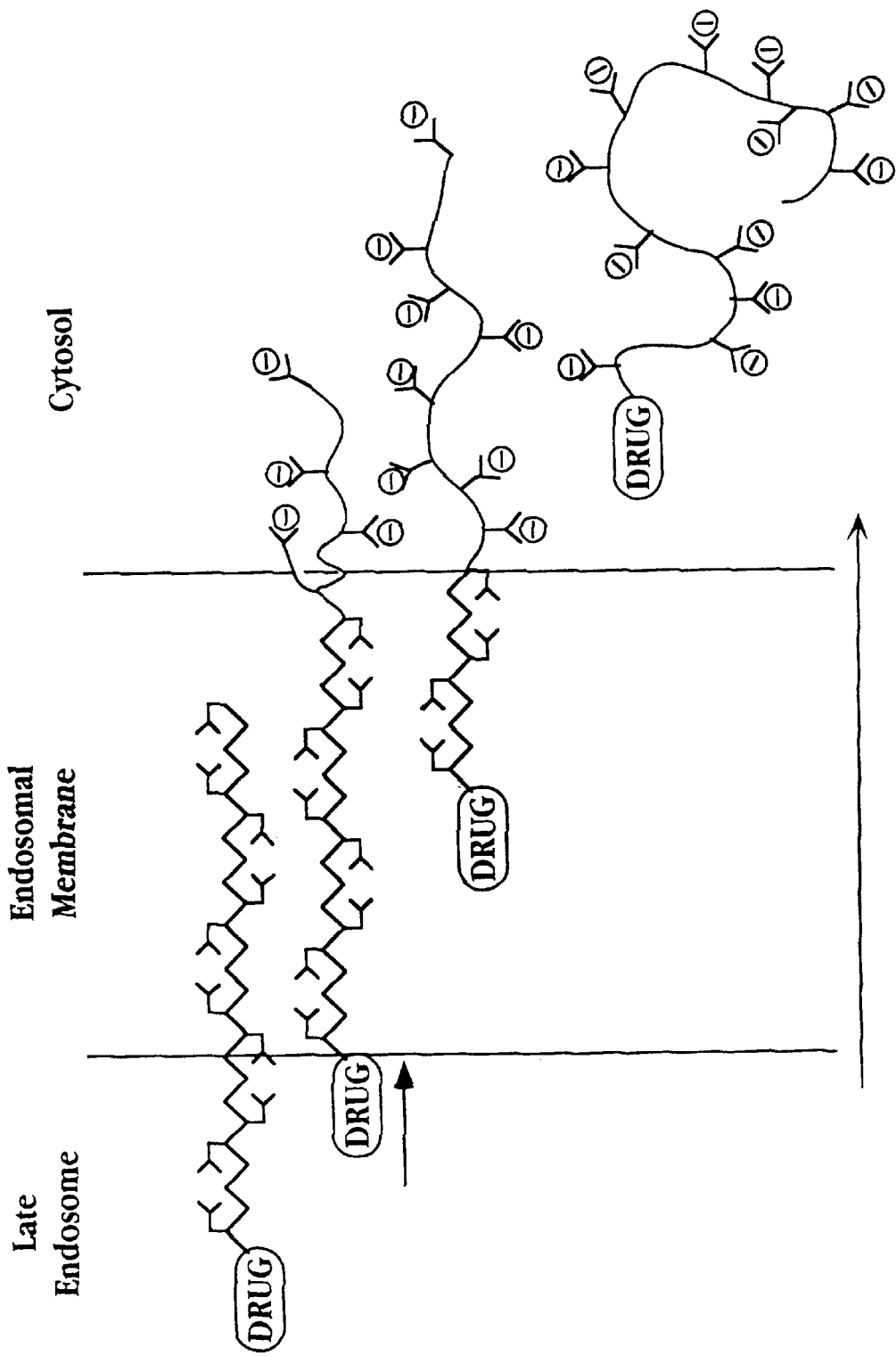
FIG. 7A shows a polypeptide functioning as a molecular engine, in accordance with an embodiment of the invention.

For delivery of particularly large and/or polar compounds, which do not diffuse across a lipid membrane at a practical rate, such delivery is facilitated when the polymer, in its α-helical conformation, is longer than the thickness of the membrane. In this case, at least a portion of the polypeptide is able to enter the cytosol and convert to its high-pH form, a process energetically favored by solvation and ionization, before the large and/or polar compound is required to enter the lipid membrane, as illustrated in FIG. 7A.

In a polypeptide a-helix, each amino acid residue contributes approximately 1.5 Å to the axial length. Since lipid bilayers of cell membranes in eukaryotic cells are typically about 33 to 36 Å thick, a preferred length for the polymer composition is about 22 amino acids or more. Several additional amino acids are preferably included to assure that at least one acid side chain enters the high-pH compartment to initiate conversion to the ionic high pH form. Thus, polypeptides in the length range of about 24 to 100 amino acids, preferably 24 to 48 amino acids, are preferred for endosome-to-cytosol transport of large and/or polar compounds.

For delivery of the smaller or less polar attached compounds, shorter peptides may be used. When the polypeptide is below, near, or even somewhat above its transition pH, the low-pH lipophilic form is present at an equilibrium concentration sufficient to effect diffusion of the polypeptide into and across the lipid membrane. Only for attached compounds which significantly interfere with this diffusion, as described above, is it necessary for the polypeptide to completely span the membrane at any given time.

As discussed further below, entry into a cell membrane is most likely to be initiated at a terminus of the polypeptide, especially for more polar polypeptides. In longer polypeptides, such as those having lengths greater than about 200 amino acids, the termini are at a low concentration and are statistically less likely to contact the cell membrane. In addition, longer polypeptides, by virtue of size alone, may not be efficiently engulfed within an endosome, which is typically about 800 Å in diameter. Preferred polypeptides, such as described above, will thus have an average length of less than 200 amino acids, and most preferably less than about 100 amino acids.

B5. Polyglutamate and Polyaspartate homopolymer components. High molecular weight, random-length polyglutamic acids, such as are commercially available from, e.g., Aldrich Chemical Co., Milwaukee, Wis., or readily polymerized from N-carboxyanhydrides (Blout), precipitate from water, but do not partition into n-pentanol, at about pH 4. Such polymers also fail to cross cell membranes in direct-entry experiments, such as described below and Example 10A, at pH's attainable in endosomes of mammalian cells. Further, when a high molecular weight poly-L-glutamic acid was linked to various anticancer drugs, such as adriamycin (Hoes, Nukui), in an effort to enhance endocytotic uptake of the drug by increasing aqueous solubility, the polyglutamic acid component of the polypeptide-drug conjugate neither entered the endosomal membrane nor transported the drug across the membrane. Rather, the carrier was degraded within the fused endosome-lysosome, and the released drug then passively diffused across the lysosomal membrane into the cytosol.

These results may be explained on the premise that relatively polar polypeptides (e.g., containing over about 50% glutamic acid residues) begin entry into cell membranes via one or the other termini of the polypeptide, as discussed further below. Because high-glutamic polypeptides with unmodified termini have a multiplicity of unshielded polar sites at both the C-terminus and the N-terminus, they are apparently unable to efficiently initiate entry into the nonpolar interior of a cell membrane.

In contrast to these results, relatively low molecular weight polypeptides, having 60–100% glutamic acid residues, when modified to provide local lipophilicity at one or both termini, as described in below, crossed cell membranes in direct-entry experiments, as described in Example 10A. Such modified high-glutamic polypeptides are also able to partition into n-pentanol from aqueous buffers at pH's in the range of 4.3–4.9.

Polyaspartic acid is soluble in aqueous solution at acidic pH, failing to partition into n-octanol or n-pentanol even when the pH of the aqueous phase is as low as 4. Polyaspartic acid also fails to cross cell membranes in direct-entry experiments, such as described in below. Such lack of lipophilicity is expected, both on the basis of partitioning calculations (Leo), and because molecular modeling of a polyaspartic acid α-helix shows that the carboxyl moieties are unable to form the double-hydrogen-bonded pairs required to shield the polar acid sites from the environment.

B6. Axial Distribution of Side Chains

In an α-helix each consecutive amino acid side chain is rotated 100° relative to the previous side chain in the polypeptide. Using this axial rotation value, a spiral plot of the axial distribution of side chains, and particularly the H-bonded acid pairs, can be constructed which provides a convenient means for assessing the relative symmetry of distribution of the side chains about the polypeptide backbone in its low-pH α-helical form. FIGS. 7B–C show the axial distribution and pH-dependent octanol/water partitioning properties of two representative polypeptides, one having an asymmetrical and the other having a symmetrical axial distribution of H-bonded acid pairs.

The results in FIG. 7B–C, plus corresponding results from a variety of other sequences indicate that peptide sequences wherein the H-bonded acid pairs are symmetrically distributed about the helical axis exhibit appreciably better octanol solubility than peptide sequences wherein the H-bonded acid pairs are asymmetrically distributed about the axis. Presumably the poor octanol solubility exhibited by polypeptides with asymmetrical axial distributions of H-bonded acid pairs is a consequence of inter-molecular interactions between their hydrophobic faces and/or between their hydrophilic faces.

C. Initiator Moiety

Two general embodiments of the initiator moiety are contemplated. The first is an initiator polypeptide sequence, which may be an end-region extension of a polypeptide component containing less than about 50% acidic residues, or, in the case of a homopolymer of acidic amino acids, a more hydrophobic, alpha-helix forming region containing less than about 50% acidic, e.g., glutamate residues. The second is a hydrophobic moiety that may be, for example, the compound to be administered, or a compound effective to eliminate and/or mask end charges and polar groups.

C1. Initiator Sequences. Further addition of lipophilic amino acids near the C-terminus of the polyglutamic acid described above (i.e., leucines at residue positions C2, C3, and C5; see FIG. 8C) afforded quite good transport across cell membranes. The polypeptide showed good solubility in n-pentanol, though not in n-octanol, at acidic pH.

Such an amino acid sequence at the polypeptide terminus is particularly useful in that it provides a short initiator sequence which is effective to form an α-helix at a higher pH than would be required for a similar length sequence of, in the present example, glutamic acid residues, to assume this conformation. Cell entry and partitioning studies have demonstrated that incorporation of such an α-helix-forming initiator sequence enhances lipid solubility and cell entry to a significantly greater extent than lipophilic modifying groups which do not in themselves initiate α-helix formation. The initiator sequence, in forming an α-helix at relatively high pH, also promotes subsequent helix propagation in the adjacent segments of the polypeptide.

Figure 8A:
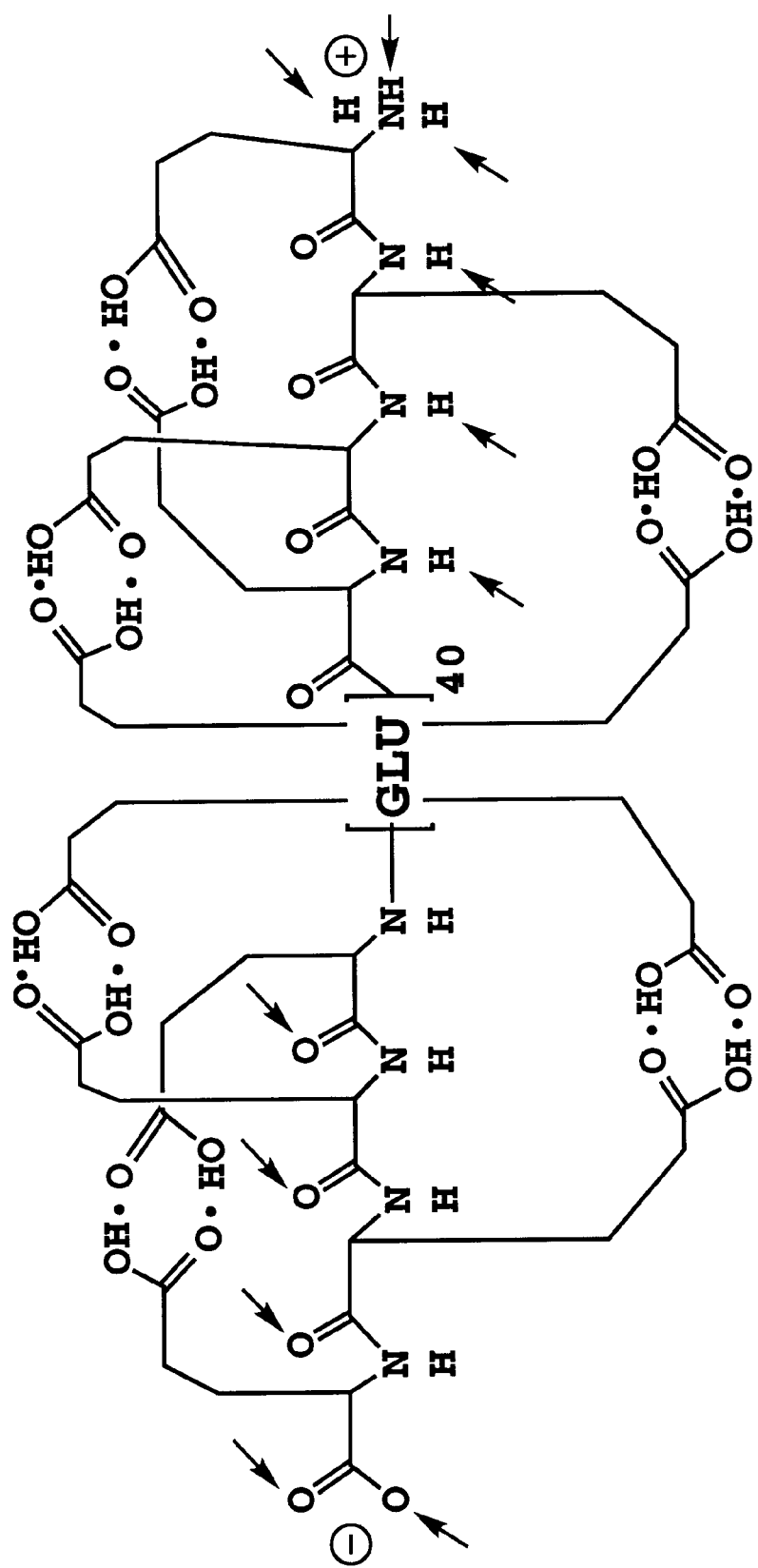
FIGS. 8A–8C depicts polypeptides assessed for octanol solubility and cell entry, where

Preferred initiator sequences are three to twelve, and preferably five to ten, amino acid residues in length, and preferably include glutamic acid, leucine, methionine, alanine, 2-aminobutyric acid, 3-aminobutyric acid, norvaline, and β-alanine, where the ratio of non-acid side chain residues to acid side chain residues is greater than 1, and preferably greater than 2. Examples of such initiator sequences are XEXXβ and XEXXXβ (C-terminal) and glutaric acid-XXEX and glutaric acid-XXXEX (N-terminal), where E is glutamic acid, β is β-alanine, and X is selected from the list above. One such C-terminal sequence, leu-glu-leu-leu-β, is shown in FIG. 8C.

Such terminal sequences provide the clearest benefit in highly polar (e.g. high glutamic) polypeptides. They are also useful in defined-sequence polypeptides containing lower levels (i.e., less than about 50%) of acid side chain residues. Such polypeptides, however, generally have a higher propensity toward α-helix formation, and thus other initiator moieties, such as a lipophilic drug at the terminus, or a shielding group as described above, may be effective to initiate entry of such polypeptides into a membrane.

C2. Shielding or Removal of Polar Sites. A polypeptide in an α-helical conformation typically contains multiple polar sites at both the C-terminus and the N-terminus which are not shielded by intramolecular hydrogen bonding. These unshielded polar and ionic sites constitute a substantial bar to initiation of polypeptides into lipid layers, due to the presence of solvated counterions and water of salvation, and the propensity of the polar termini to assume a non-α-helical conformation. Deleting the terminal charge and shielding or removing one or more of these polar sites can improve lipid solubility, particularly in the case of short or highly polar polypeptides, such as high-glutamic polypeptides, described above.

A lipophilic substance, such as a drug to be delivered, attached at a polymer terminus eliminates the charge at said terminus and provides local lipophilicity. Deleting the terminal charge and shielding or removal of polar sites can also be accomplished by incorporating, at the C-terminus or the N-terminus of a polypeptide, a group which covalently bonds to, or includes, the terminal carboxyl or amino group, respectively, and which further contains at least one remote polar group, such as a hydroxyl or carbonyl group, which is effective to shield, by hydrogen bonding, one or more additional polar groups at or near the polypeptide terminus. Specific examples follow.

Figure 5A:
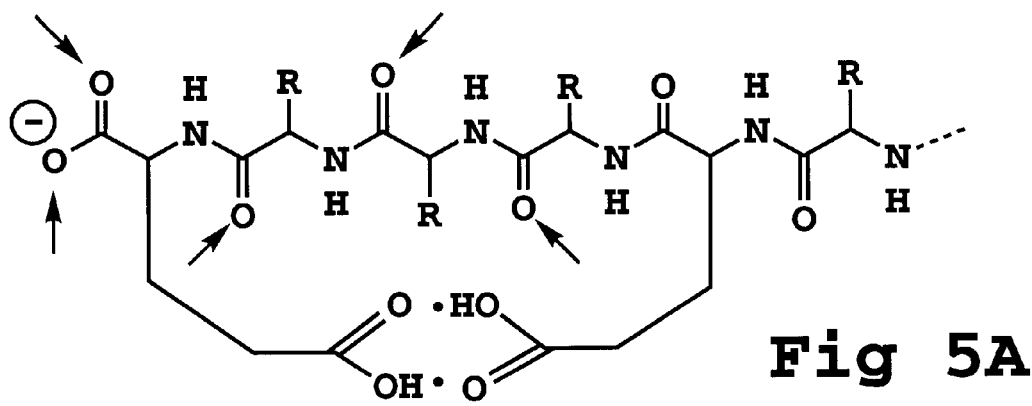
FIGS. 5A–5C show representative C-terminal end structures of polypeptides, where the structures in 5B–5C have partially shielded or deleted terminal polar sites.
Figure 5B:
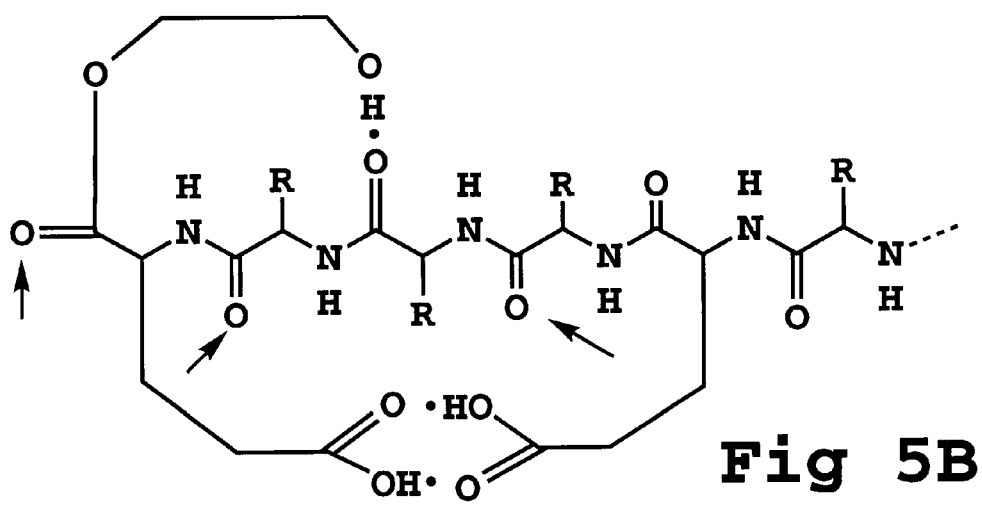

C-Terminus shielding. The C-terminus of a polypeptide typically contains three carbonyl groups and a negatively-charged carboxylate ion which are not shielded by intramolecular hydrogen bonding, as illustrated in FIG. 5A. One method for reducing the number of these unshielded terminal polar sites is to incorporate an α-ester, preferably a 2-hydroxyethyl ester, at the C-terminus, as illustrated in FIG. 5E. Polar sites may also be conveniently eliminated from the C-terminus by initiating the synthesis of the polypeptide on a support resin with β-alanine, as shown in FIG. 5C, and as described in Example 1.

Figure 6C:
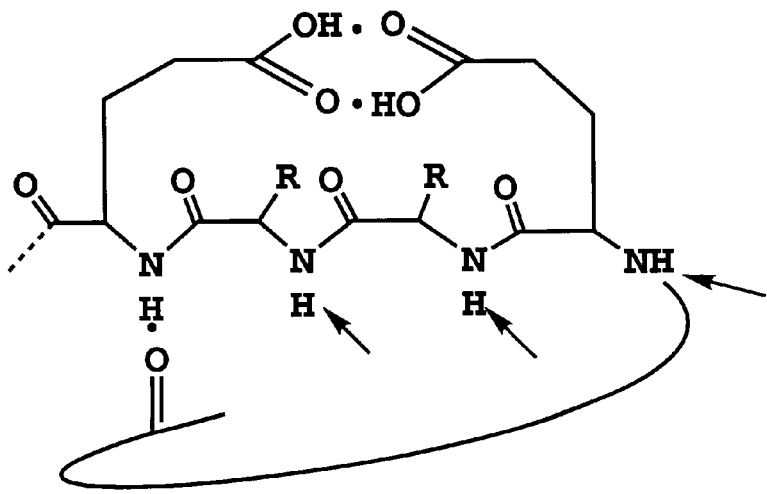
Figure 6D:
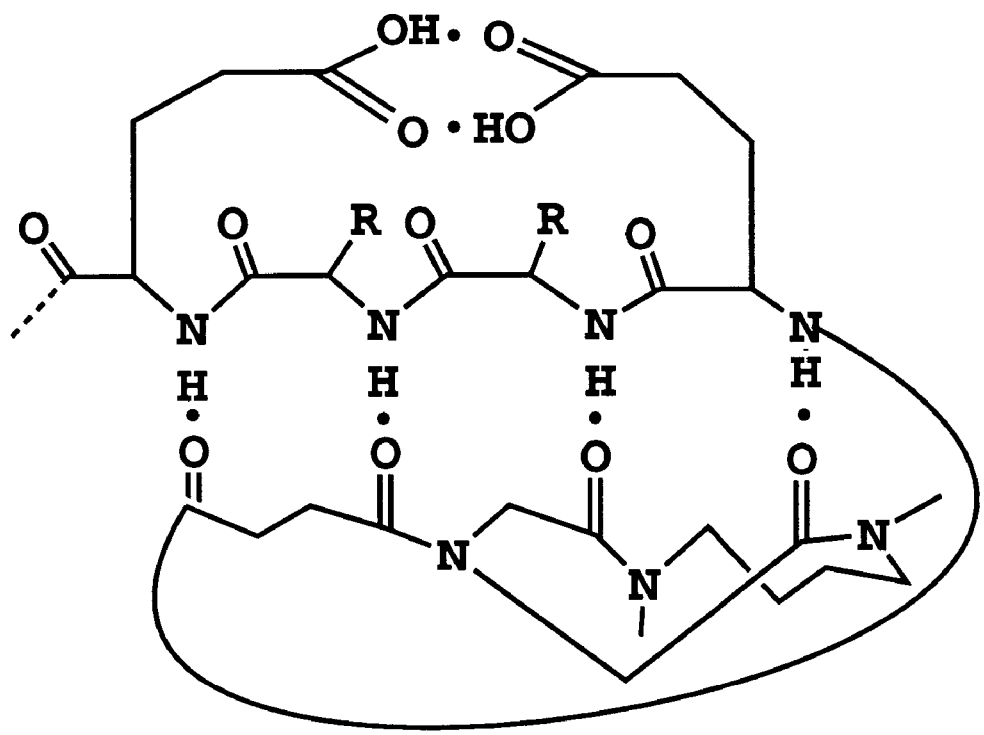
Figure 6E:
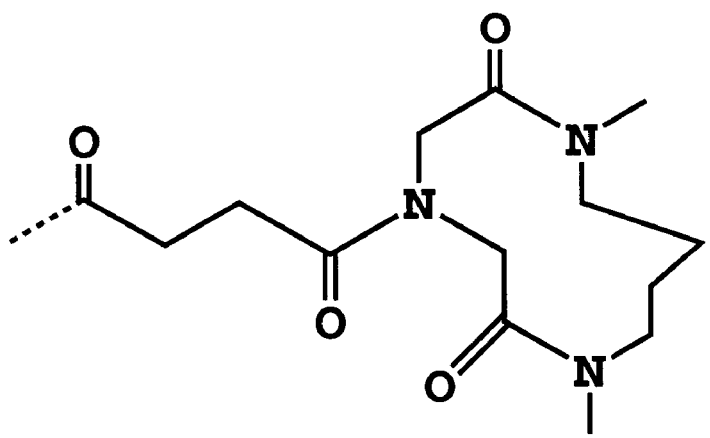
FIG. 6E shows an "N-crown" structure which may be used to shield polar sites of N-terminal end structures in polypeptides, as shown in FIG. 6D.

N-Terminus shielding. The N-terminus of a polypeptide typically contains three amide protons and a positively-charged protonated amine which are not shielded by intramolecular hydrogen bonding, as illustrated in FIG. 6A. Polar sites may be conveniently removed from the N-terminus by terminating the polypeptide with a diacid, as illustrated in FIG. 6B. Alternatively, polar sites can be shielded simply by acetylating the terminal amine, as illustrated in FIG. 6C. Hydrogen bonding occurs as shown when the polypeptide is in an a-helix. More extensive shielding of the N-terminus may be achieved by a novel structure, referred to as an N-crown, designed to shield all of the normally-exposed polar sites at the N-terminus of α-helices. FIG. 6D shows one such N-crown, whose structure is given in FIG. 6E, in the H-bonded conformation it is believed to adopt when linked to the N-terminus of a polypeptide existing in an α-helical conformation.

Figure 8B:
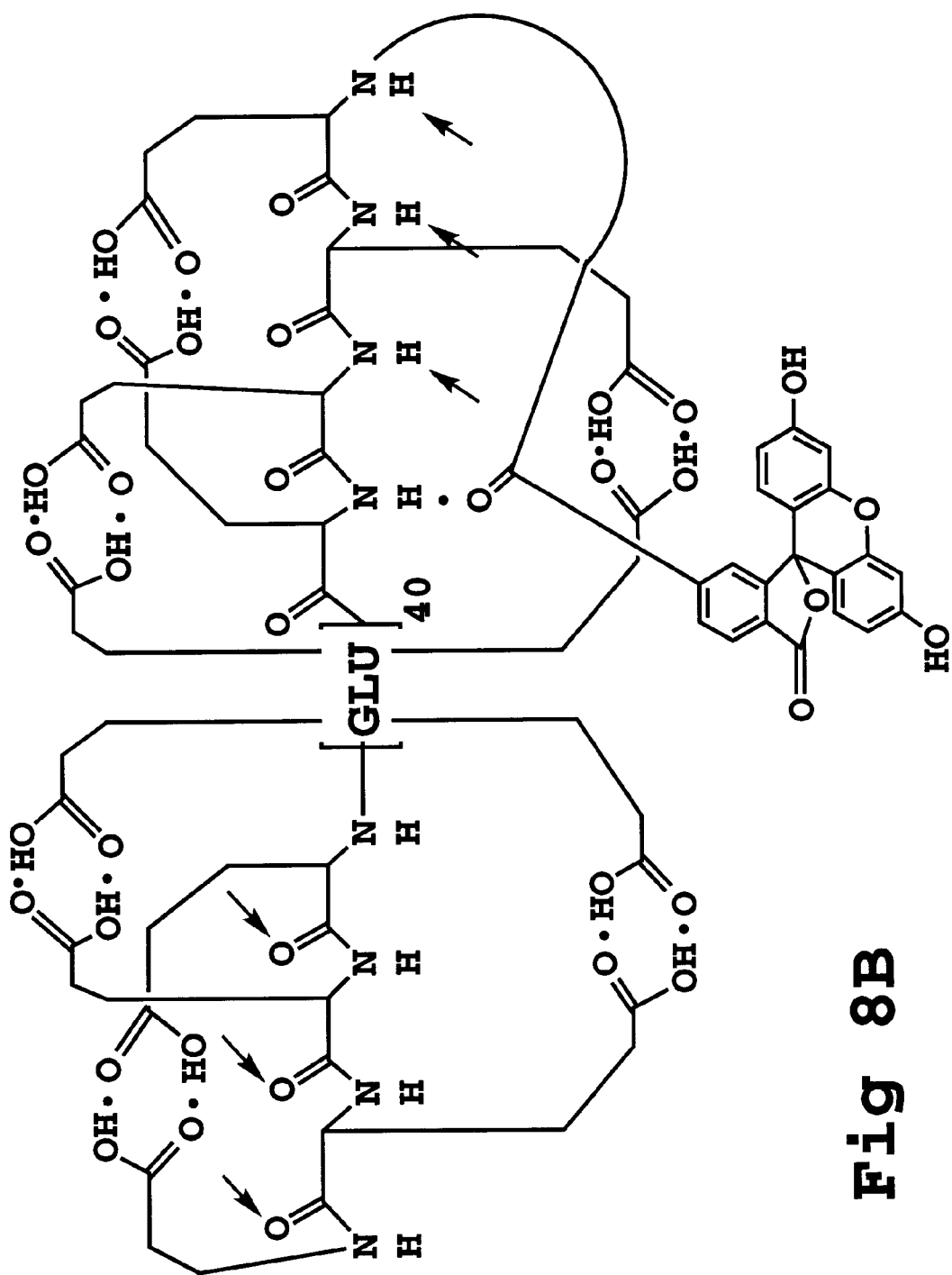
Figure 8C:
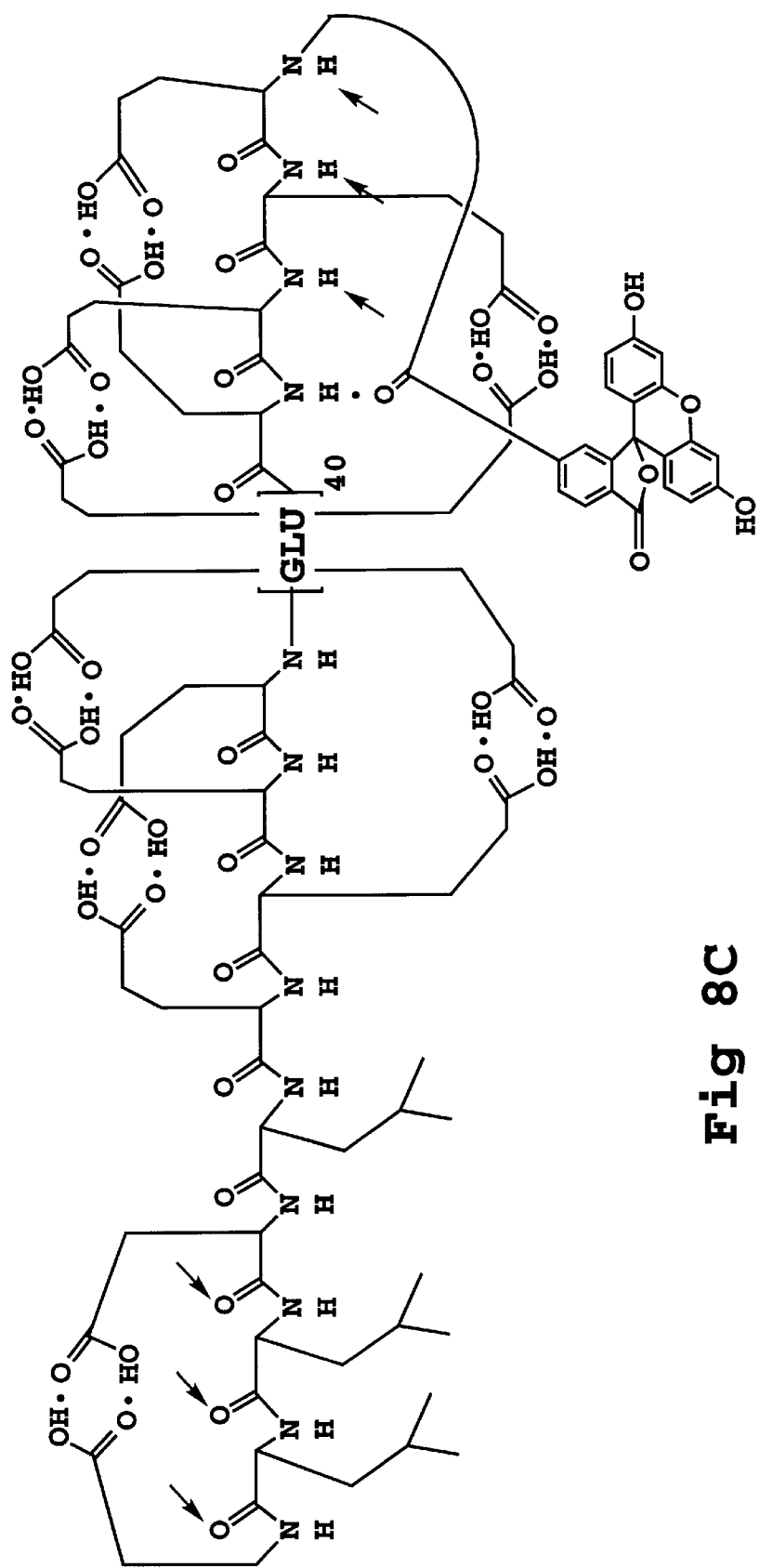

A polyglutamic acid having such modifications is shown in FIG. 8B. The unmodified polypeptide, shown in FIG. 8A, did not partition into n-octanol or n-pentanol, nor did it show any transport across cell membranes in direct entry studies.

Figure 10:
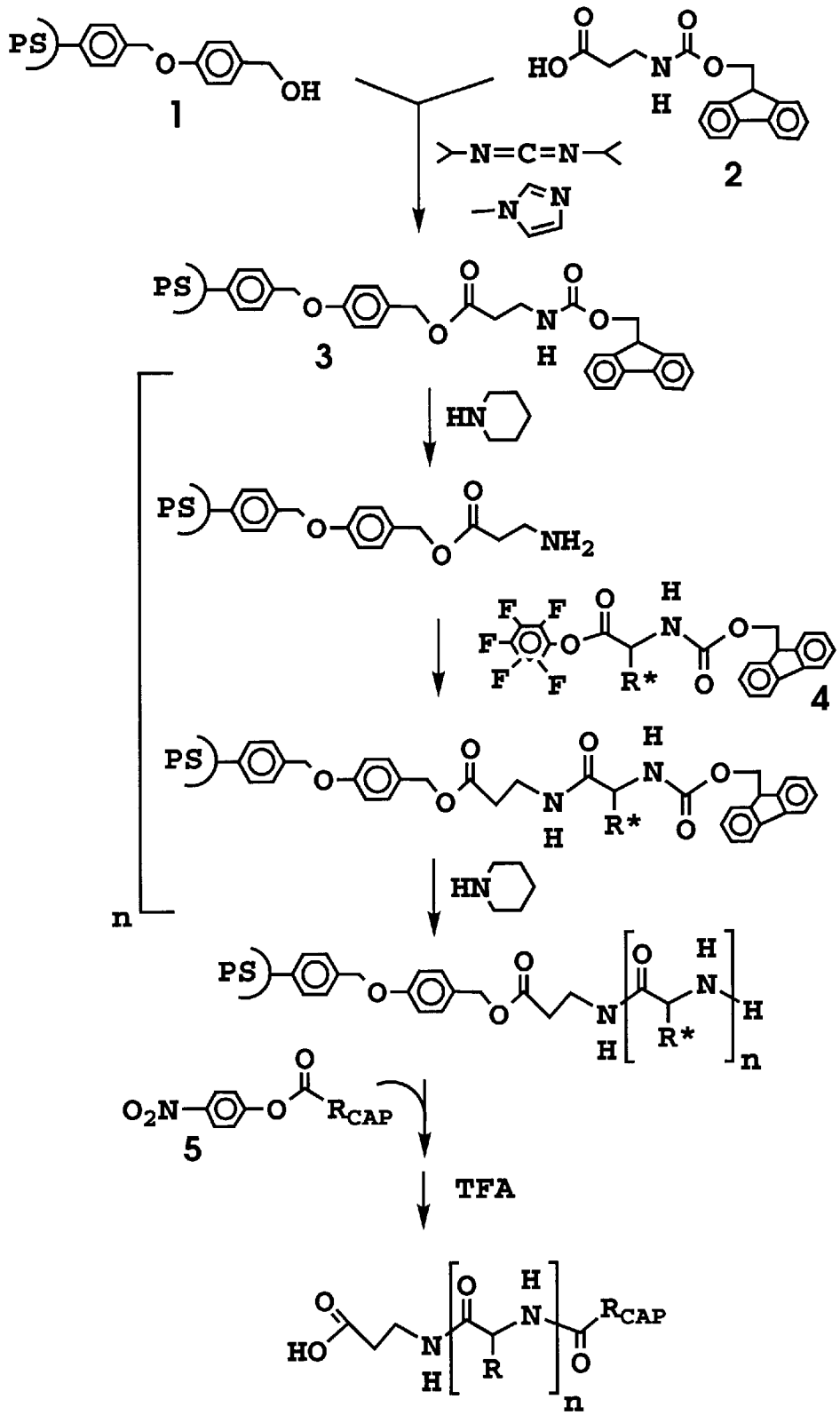
FIG. 10 shows a method of preparation of polypeptides which may be used in accordance with the invention.

Addition of an N-terminal carboxy-fluorescein, as shown in FIG. 8B, removes the positive charge from the N-terminus, partially shields N-terminal polar sites, and adds a large lipophilic moiety (i.e., fluorescein in its low-pH form) to the N-terminus. In addition, the negatively charged carboxylate, with two polar sites, was eliminated from the C-terminus by initiating the polypeptide synthesis with a β-alanine, as shown in FIG. 10. These modifications afforded modest transport across cell membranes (FIG. 8B), and the polypeptide partitioned into n-pentanol, but not into n-octanol.

In operation, once the initiator moiety at the terminus of a polypeptide has entered the membrane, succeeding segments of the polypeptide are able to convert to a lipophilic, hydrogen-bonded conformation. Such conversion is driven by the increasingly acidic environment within the endosome, as well as the increased local lipophilicity provided by the adjacent α-helical segments of the polypeptide and the proximity of the cell membrane.

After entry of the initiator moiety, a polypeptide having a large number of acid side chains is able to partition into the membrane in a "stepwise" manner, in which an acid side chain positioned immediately adjacent to the membrane forms a hydrogen-bonded pair with a nearby acid side chain, and the segment of the polypeptide containing this pair, having assumed a lipophilic α-helical conformation, enters the membrane.

In this sense, the spacing between carboxylic acid side chains is of particular importance. When a polypeptide enters a membrane in the stepwise manner described above, a carboxylate side chain adjacent to the membrane which is unable to pair with another carboxylate side chain is likely to block further entry. As noted above, spacings of zero, two or three amino acids are effective for such pairing. Further, if drugs are to be attached at sites along the polypeptide chain, rather than only at the termini, they must be located so as not to interfere with said spacing and pairing between side chain carboxylates. Thus, random attachment of drugs, as well as random spacing of non-acid side chain residues, including glutamic esters, should be avoided.

As described further below, additional motive force for unidirectional transport is provided by ionization and hydration of the side-chain carboxyls once the polypeptide spans the membrane and encounters the higher-pH cellular cytosol. Thus a polypeptide having a high percentage of side chain carboxyls is expected to provide a high driving force to transport an attached compound across the membrane.

Accordingly, one preferred class of polypeptides for use in the present invention includes those having 30%–100%, and preferably 50%–100%, glutamic acid content, and having an initiator sequence as described herein at one terminus. (In this context, 100% glutamic acid content refers to the central chain of the polypeptide, excluding the initiator moiety.) Preferably, the compound to be transported is attached at or near the other terminus of the polypeptide.

D. Transition pH

The pH at which the polypeptide component, or a segment thereof, converts between its hydrophilic and lipophilic forms, and is effective to partition from an aqueous to a lipid phase, or vice versa, is referred to as the "transition pH". In general, for transporting a compound from a low-pH environment across a lipid layer to a higher-pH aqueous compartment, this conversion should occur at a pH greater than or approximately equal to the pH of the low-pH environment, and less than the pH of the higher-pH aqueous compartment.

It will be understood, however, from the previous discussion, that local modifications of a polypeptide can facilitate entry and partitioning into a lipid layer at a pH greater than that at which the polypeptide as a whole would convert to an α-helical conformation in the absence of such modifications, or in the absence of a lipid layer. Transport through a thin lipid layer, such as a membrane, to an aqueous compartment is also facilitated by ionization and solvation as the composition converts back to a hydrophilic conformation upon contacting said aqueous compartment. Therefore, the pH at which a composition effectively transports in vivo, or in cell entry studies, may differ from the transition pH of the polypeptide molecule in two-phase partitioning studies. The latter value thus serves as a useful guideline for initial selection of polypeptides, but should be supplemented by direct entry studies, described below, particularly for highly polar polypeptides.

Effective transition pH varies for different applications. For instance, the bacterium *H. pylori*, a major cause of ulcers, exists in a very acidic environment in the stomach. This environment may be specifically targeted, as discussed below, by the use of a polymer composition which is effective to partition into a lipid layer at a pH of about 4.5 or less.

In contrast, for transdermal delivery, it is preferred that: a) the polymer composition exists in its lipophilic form at a pH safely achievable in the extracellular lipid matrix of the stratum corneum, and b) the polymer composition converts to its hydrophilic form on contacting the aqueous environment underlying the stratum corneum. A transition pH in the range of about 5 to 6.5 generally satisfies these two criteria.

In transport of relatively polar compounds from the endosome to the cytosol of eukaryotic cells, a polymer composition as described herein can function as a molecular engine, pulling the relatively polar compound into and through the endosomal membrane. The motive force exerted by the engine is generated as the non-ionic lipophilic α-helical polypeptide undergoes ionization and solvation at the cytosolic face of the endosomal membrane, as illustrated in FIG. 7A. This motive force is, in part, a function of the difference between the transition pH and the pH of the cytosol. Thus, the lower the transition pH, the more power such an engine should exert, and hence the greater the load it can transport through the endosomal membrane. For compounds which are fairly small and/or of only moderate polarity, the polymer composition used for endosome-to-cytosol transport may have a fairly high transition pH, such as in the range of 6.4 to 6.8. For larger and/or more polar compounds (i.e., greater loads), the transition pH should generally be lower.

However, if the transition pH is too low, endosome/lysosome fusion can occur before the polypeptide engine converts to its lipophilic form and enters the encompassing membrane, leading to enzymatic degradation of the polypeptide (assuming it comprises L-amino acids) before it can carry out its transport function. At the time of endosome/lysosome fusion, the pH of the endosome is typically in the range of about 5 to 6. Thus, a minimum transition pH in this range is preferred for compositions assembled from L-amino acids and intended for endocytotic entry.

From the above, it is seen that the optimal transition pH can vary substantially depending on the compound to be delivered and the compartment from and into which it is to be delivered. Several parameters, described below, can be varied to adjust the transition pH over a broad pH range, thereby allowing optimization of a polymer composition for delivery of a selected compound between selected compartments.

1.) Length. As shown in Table 2A, there is a modest increase in the transition pH, as determined in an octanol/water partitioning system, as the length of the polypeptide is increased.

2.) Acid Amino Acids. The results in Table 2B demonstrate that, as a rule, glutamic acid residues provide a higher transition pH than do aspartic acid residues. Results in this table also demonstrate that the order and spacing (e.g., ELLDL versus ELLLD) also have a significant impact on the transition pH.

3.) Non-Acid Amino Acids. The results in Table 2C demonstrate that selection of non-acid amino acid moieties can also substantially affect the transition pH. For example, replacing leucines with phenylalanines reduces the transition pH. As shown in Table 2C, the transition pH also is reduced further by each replacement in the series: leucine→valine→alanine→glycine (data for glycine not shown). Thus, one simple method of adjusting the transition pH over a broad range is by progressively replacing leucine residues (which give high transition pH values) with alanines. It is also seen that leucines give about the same transition pH values as norleucines.

4.) Ratio of Acids to Non-Acids. It was found that the transition pH is generally reduced as the proportion of acid amino acids, replacing lipophilic amino acids such as leucine, is increased.

5.) End Structure. Masking or deleting polar end groups not engaged in hydrogen bonding serves to increase the transition pH.

TABLE 2

|   | Repeating Sequence | Length | Transition pH* |
|---|---|---|---|
| A. | Length: | | |
|   | -ELALE- | 25 | 5.83 |
|   | -ELALE- | 45 | 6.05 |
|   | -ELALE- | 65 | 6.14 |
| B. | Acid Amino Acids: | | |
|   | -ELLLE- | 50 | 6.92 |
|   | -ELLLD- | 50 | 6.51 |
|   | -DLLLE- | 60 | 6.45 |
|   | -ELLEL- | 49 | 6.85 |
|   | -ELLDL- | 49 | 6.29 |
| C. | Non-Acid Amino Acids: | | |
|   | -ELEDLDLL- | 54 | 5.50 |
|   | -EFEDLDLL- | 54 | 5.39 |
|   | -ELLLE- | 50 | 6.92 |
|   | -ELVLE- | 50 | 6.44 |
|   | -ELALE- | 50 | 6.14 |
|   | -ELLLE- | 30 | 6.83 |
|   | -ELALE- | 30 | 5.90 |
|   | -EALAE- | 30 | 5.10 |
|   | -ELLLE- | 30 | 6.93 |
|   | -EnLnLnLE | 30 | 6.90 |

A = alanine
D = aspartic acid
E = glutamic acid
F = phenylalanine
L = leucine
nL = norleucine
V = valine
*As determined in n-octanol/water Table 2 shows a selection of transition pH's attained in an n-octanol/water partitioning system by varying the structural features discussed above. By further adjusting these parameters, it is possible to prepare polypeptides with still higher or lower transition pH's. For example, a composition with a transition pH of 4 or lower may be prepared by including a high proportion of aspartic acid and alanine subunits in a relatively short polypeptide.

As stated above, transition pH's determined from octanol/water or pentanol/water partitioning studies provide a useful guideline for selecting appropriate polypeptides for delivery of a compound to a selected environment. However, it will be appreciated that additional factors may influence the behavior of the polypeptide in a cellular environment. Studies have suggested, for example, that polypeptides containing high levels of leucine may bind to serum proteins. It has also been demonstrated herein that a polypeptide having local regions of lipophilicity at the termini may undergo a transition effective for cell entry in vitro or in vivo at a pH higher than that shown in bulk partitioning studies. Therefore, partitioning studies are ideally followed by in vitro cell entry experiments, as described below, to further assess the membrane transport properties of a composition. A candidate polypeptide may also be tested for binding to serum proteins by performing electrophoresis on agarose gels with and without added serum albumin.

E. Coupling of Compound to Polypeptide Component

One or more drugs or other compounds can be attached to the polypeptide through sites at the termini and/or at a limited number of selected sites within the chain. As discussed above, random attachment or high loading of compounds along the chain can impede partitioning into the membrane, especially for high acid side chain polypeptides.

Figure 9:
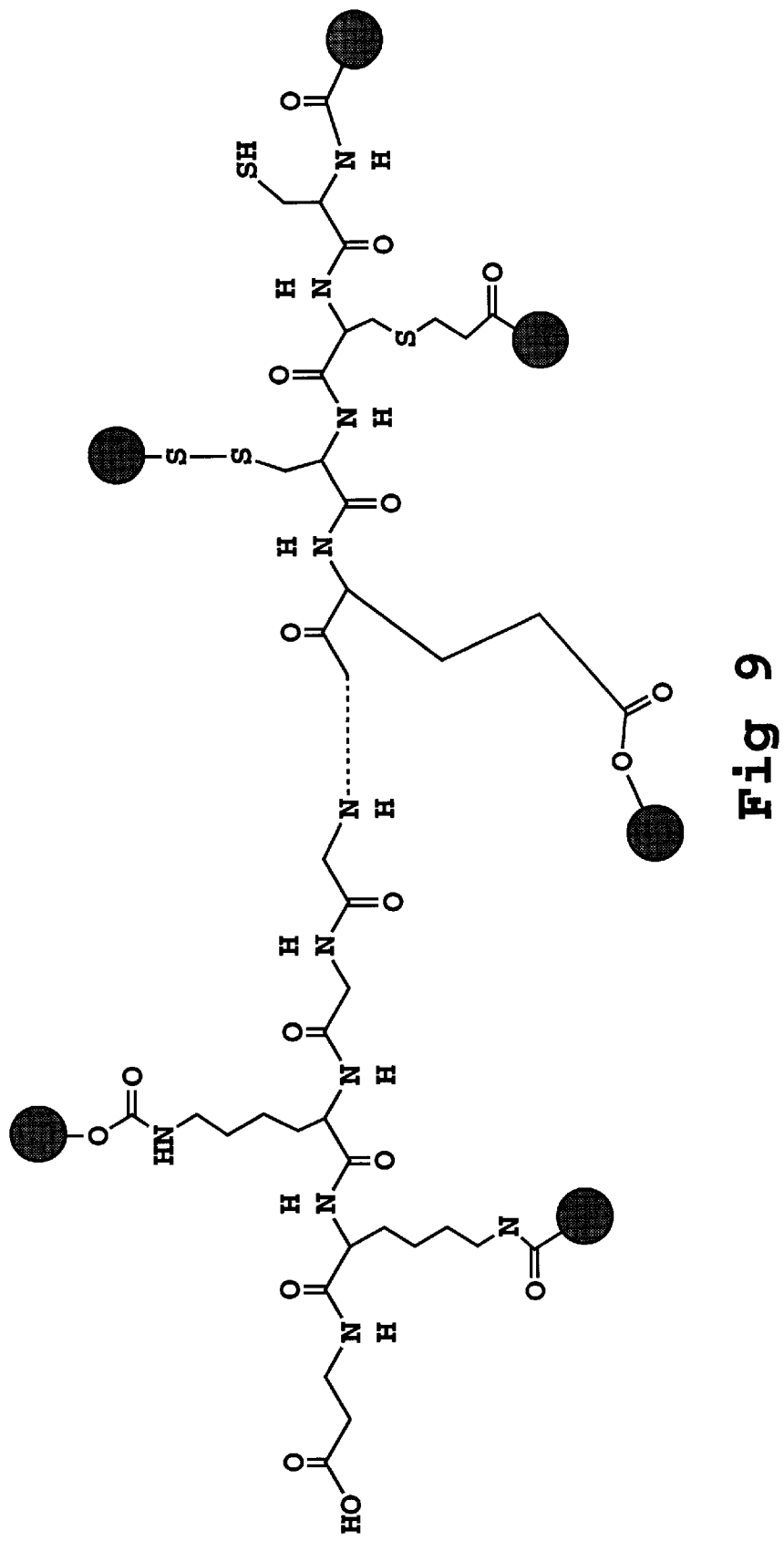
FIG. 9 illustrates representative sites of side-chain attachment on a polypeptide, showing, from left to right, amide and carbamate links to lysine, an ester link to glutamic acid, and disulfide, thioether, and amide links to cysteine.

Methods for selective attachment are well known in the art, and several such methods are described in Examples 2–7, below. FIG. 9 shows representative linkage positions and types which are both convenient and effective for a substantial variety of compounds and polymer compositions. Shown, from left to right, are amide and carbamate links to lysine, an ester link to glutamic acid, and disulfide, thioether, and amide links to cysteine. In particular, linkages selected from amide, carbamate, ester, thioether, disulfide, and hydrazone are typically easy to form and suitable for most applications. Ester and disulfide linkages are especially preferred if the linkage is to be readily cleaved in the cytosol after delivery of the compound.

Figure 11A:
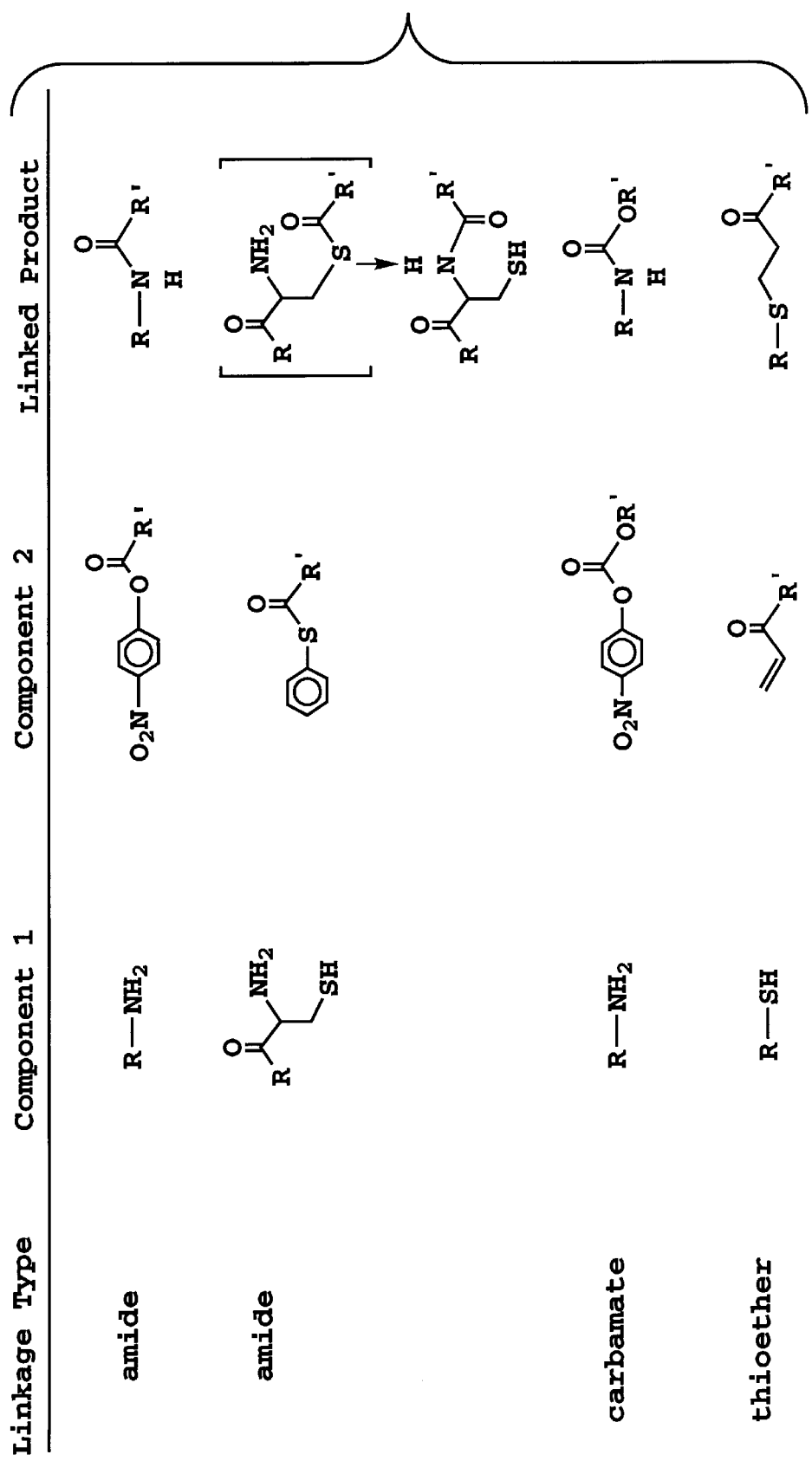
FIGS. 11A–11B show representative polymer-compound linkages, such as may be used in attaching a compound to a side chain or terminus of a polypeptide.
Figure 11B:
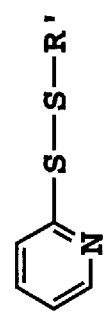

FIG. 11 illustrates representative starting materials and products of such linkages. Examples 2–7 describe the linkage of representative compounds, including cyclosporin, Taxol™ (paclitaxel), and a Morpholino antisense oligomer (Summerton and Weller) to representative polymers via these linkage types. Cyclosporin is linked to a polypeptide via a disulfide linkage (Example 3A), a thioether linkage (Example 4A), a carbamate linkage (Example 5), and an amide or thioether linkage (Example 6). Also described are corresponding linkages of Taxol™ to a polypeptide using similar methods (Examples 3B, 4B, 5, and 6B, and 7A) and an amide linkage to a Morpholino antisense oligomer (Example 6C, shown in FIG. 13A–C).

In the above examples, Taxol™ is conveniently linked to the polypeptide via its C-7 hydroxyl group. For linking cyclosporin A, metabolite 17, which has a primary hydroxyl group (Eberle and Nuninger, 1992), is used. In both these cases, the linkage does not involve known active sites of the molecule. Other drugs that may be used in applications described below, such as metronidazole or doxorubicin, also have primary hydroxyl groups for convenient attachment. In general, numerous functional groups (hydroxyl, amino, halogen, etc.) may be used for attachment. Groups which are not known to be part of an active site of the compound are preferred, particularly if the polypeptide or any portion thereof is to remain attached to the compound after delivery.

Example 8 describes representative methods for purification of polymer-compound products, as well as methods for structural analysis of said products.

The compound/polypeptide ratio is preferably 5:1 or less, and more preferably 1:1 for large and/or polar compounds. The compound is preferably attached at or near a terminus of the polypeptide; most preferably, one terminus includes an initiator moiety and the other an attached compound.

For especially large and/or polar compounds, such as a nucleic acid binding polymer, transport may be enhanced by attaching multiple, e.g. 2 to 5, polypeptide carriers of the invention to a single compound molecule. The carriers are preferably attached to the same region of the molecule to be transported, e.g. at or near the nucleic acid binding polymer.

III. Assessment of Composition Properties

A. Partitioning Properties

The partitioning of a compound between water and n-octanol has commonly been used in pharmaceutical research to estimate the partitioning of that compound between an aqueous compartment and a lipid bilayer of a cell membrane. Partitioning between n-octanol and a series of buffers of varying pH was used to provide a quantitative measure of the pH-dependent solubility properties of polymer compositions of the invention having acid side chain acid content of up to about 50% of the amino acids. For polymer compositions having over 50% acid side chain content, partitioning between n-pentanol and aqueous buffers was used. It should be noted that transition pH values obtained in n-octanol/water are about 0.3 pH units lower than those obtained in n-pentanol/water.

At its transition pH, a polymer partitions at equal concentrations in the aqueous and organic phases. Transition pH values determined from these studies afford a simple quantitative assessment of the effects of different factors on polymer solubility properties. Example 9 describes a convenient procedure for carrying out such a partitioning study and obtaining a transition pH value for a representative polymer composition. In this procedure, a polypeptide tagged with fluorescein is partitioned between n-octanol or n-pentanol and aqueous buffers of various pH, and the absorbance of each phase is measured. FIGS. 14A–F show plots of these absorbance values as a function of pH for six representative fluorescein-tagged polypeptide compositions of the invention, where the six different polypeptides exhibit octanol/water transition pH values ranging from 5.1 to 6.9.

Results from experiments with cultured cells, described in the next section, suggest that for polymers with up to about 50% acid amino acid composition, these partitioning properties are generally predictive of the polymer's ability to enter a lipid layer when the polymer is in its low-pH conformation. Polymers with greater than 50% acid amino acid composition, when modified to produce end group lipophilicity as discussed above, tend to show more efficient direct cell entry, at higher pH, than predicted from the transition pH shown in partitioning studies.

B. Cytosolic Entry

B1. Direct Entry. In screening polymer compositions for delivery of a selected compound, direct transmembrane passage can be assessed by brief stepwise reduction of the pH of the extracellular medium, which emulates the progressive pH reduction which occurs in an endosome due to the action of proton pumps embedded in its membrane. The process is also representative of direct entry in vivo when the pH of the extracellular medium is lower than the pH of the cytosol of the cells.

In a eukaryotic cell, when a fluorescent compound is restricted to the endosomal/lysosomal compartment, fluorescence microscopy shows a perinuclear punctate pattern in the cell. In contrast, when a fluorescent compound enters the cytosol, one sees diffuse fluorescence throughout the cell. Accordingly, linking a fluorescent tag to the compound to be transported into the cytosol allows one to readily assess subcellular localization of the polymer-compound product after its addition to cultured cells. Ideally, the linked fluorescent tag should have minimal impact on the transport process. Specifically, it should be relatively small, and it should be reasonably soluble in octanol and lipid layers at low pH and reasonably soluble in aqueous solutions at neutral pH and above. Two fluorescent tags suitable for most such applications are 5-carboxy-fluorescein and 7-dimethylaminocoumarin-4-acetic acid (obtained from Molecular Probes Inc., Eugene, Ore.).

Example 10A describes a direct-cell-entry experiment with cultured eukaryotic cells. In this experiment, cells were treated for a few minutes with a representative polymer composition of the invention tagged with 5-carboxyfluorescein. When the extracellular medium was neutral, no cytosolic entry was observed. However, when the pH of the extracellular medium was reduced stepwise to emulate the progressive pH reduction which occurs in the endosome, the polymer was seen to rapidly enter the cytosolic compartment, evidenced by diffuse fluorescence throughout the cells.

B2. Entry via Endocytosis

After direct-cell-entry studies have demonstrated that one or more polymers are effective for transmembrane delivery of a selected compound, cell entry via endocytosis may be assessed by methods such as that described in Example 10.

FIG. 2 illustrates the entry of a polymer-compound composition of the invention into the cytosol of a eukaryotic cell by endocytotic uptake. From the figure, it is seen that entry into the cytosol of eukaryotic cells comprises multiple steps, principal of which are the initial endocytotic uptake and the subsequent transmembrane passage from the acidified endosome to the neutral cytosol.

When a fluorescent-tagged polypeptide is endocytosed into cells, observation of a perinuclear punctate pattern indicates that the tagged material is localized in the endosomal or endosomal/lysosomal compartment. Thus, a diffuse fluorescence throughout the cell could indicate that the polypeptide achieved the desired endosome to cytosol transport. However, in the case of a polypeptide assembled from L-amino acids, such a pattern could also indicate that the polypeptide was degraded by lysosomal enzymes and only the fluorescent tag diffused into the cytosol. Therefore, it is preferable that cytosolic entry of such polypeptides via an endocytotic route be assessed by a functional assay for the drug component of the polypeptide-drug product, as described in Example 10.

Alternatively, initial endocytotic entry studies, directed toward demonstrating and optimizing endocytotic delivery of selected polypeptides, can be carried out with polymers assembled from D-amino acids, which are not degraded by lysosomal enzymes. Studies in support of the invention have shown that D- and L-polypeptides having the same sequence exhibit the same partitioning and membrane transport properties.

In this Example, the compound linked to the polypeptide is a sequence-specific nucleic acid-binding polymer, specifically, a nonionic antisense oligomer (Summerton and Weller) targeted against a specific messenger RNA for firefly luciferase, coded by a plasmid contained in the treated cells. If the antisense oligomer gains access to the cytosolic compartment of the transfected cells, a significant reduction in luciferase activity upon dexamethasone induction, relative to untreated cells, should be observed.

The polymer-compound composition was contacted with cells for a period of time appropriate for endocytotic uptake, about 5 hours. Also tested were the polypeptide alone, the antisense oligo alone, and the medium alone (control). As described in the example, the antisense oligo alone failed to inhibit its targeted messenger RNA, presumably because it was unable to enter the cytosol of the cells. In contrast, the same antisense oligo linked to the polymer of the invention inhibited luciferase activity by about 31% relative to the control, suggesting successful delivery of the compound into the cytosolic compartment.

Enhancement of Endocytosis by an Attached Affinity Moiety. The polymer compositions of the invention carry a relatively high density of negative charges in the essentially neutral extracellular medium. Further, due in substantial part to the sialic acid residues on the glycocalyx, the outer surface of a eukaryotic cell also typically carries a substantial density of negative charges. Possibly because of electrostatic repulsion between the like-charged polymer and cell surface, the rate of cell entry of some polymer-compound products via fluid-phase endocytosis appears to be relatively slow.

Further experimental results, described below, suggest that the rate of endocytosis can often be enhanced by using a moiety with an affinity for cell surfaces, such as a lipid anchor (i.e., a lipophilic molecule such as a fatty acid, long-chain alkyl amine, long-chain alcohol, etc.) linked to or complexed with the polymer-compound composition. Such lipid anchors likely serve to increase the concentration of the polymer-compound at the cell surface, such that upon invagination of the cell membrane to form the endosome, a larger amount of polymer-compound is enveloped therein than would otherwise be the case.

Where the lipid anchor is bound to the polymer via electrostatic attraction, such attraction will be eliminated at low pH, i.e. within the late stage endosome. In cases where the lipid anchor is covalently linked to the polymer-compound, it is generally desirable that the linkage be cleavable in the cytosol of cells so that the polymer-compound is released free in the cytosol rather than remaining linked to the lipid anchor embedded in the endosomal membrane.

Figure 12:
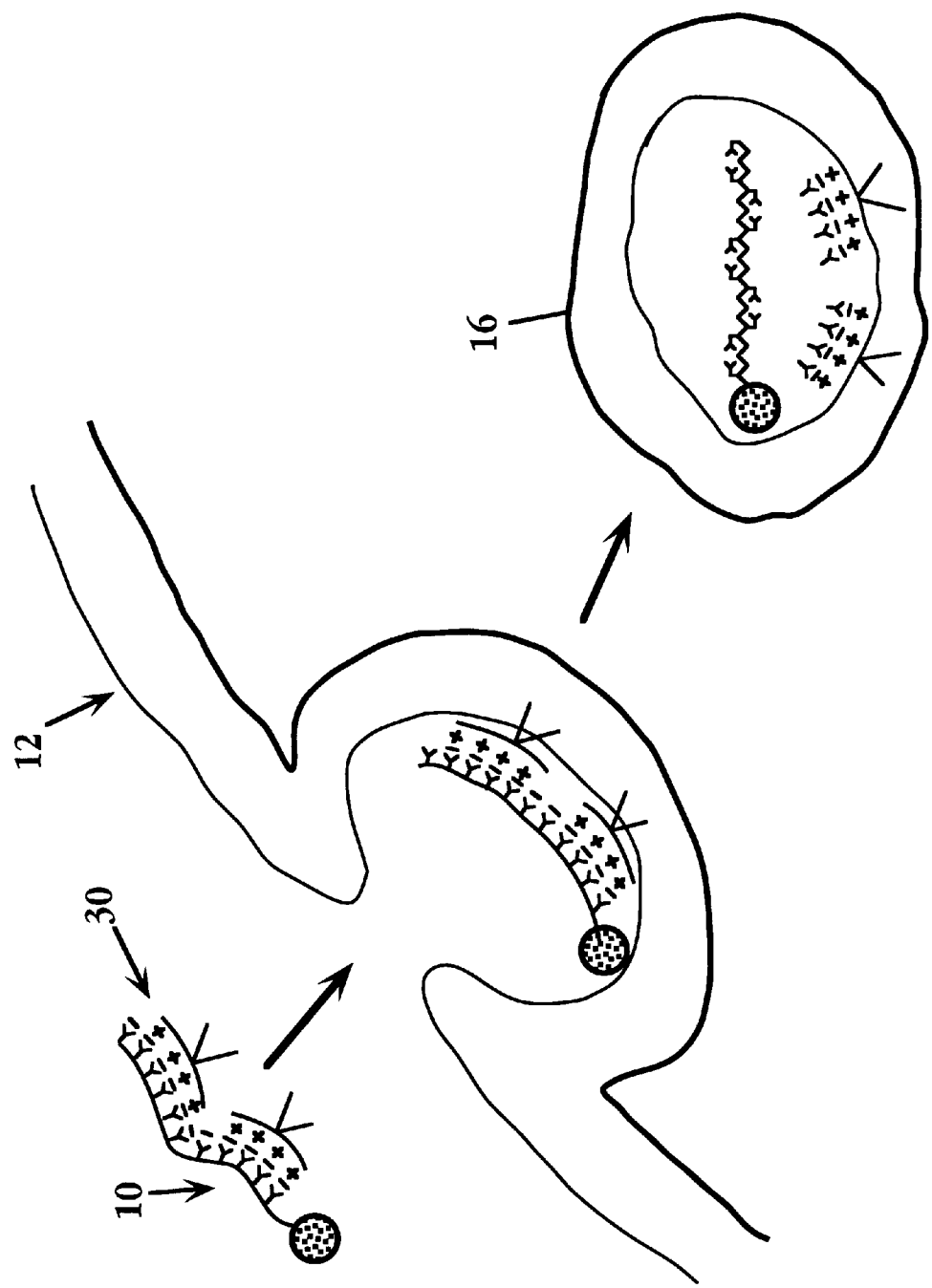
FIG. 12 illustrates enhancement of endocytosis, as shown in FIG. 2A, by a lipid anchor attached to a polycationic head group.

In a further experiment, also described in Example 10, using the polypeptide-antisense oligo composition described above, a tetracationic lipid anchor (Transfectam™, from Promega Corp., Madison, Wis., USA) was added to enhance the endocytosis step by complexing with the polyanionic polymer composition. This is illustrated in FIG. 12, where the lipid anchor is shown at 30. In this case, luciferase activity was inhibited by about 68% relative to the control, compared to 31%, above, without the lipid anchor.

FIG. 12 illustrates the likely role that a lipid anchor such as Transfectam™ plays in enhancing the initial endocytotic step, followed by its dissociation from the polymer when the polymer converts to its low-pH non-ionic form in the late-stage endosome.

It should be appreciated that numerous compounds, such as lipophilic drugs (e.g., Taxol™ and cyclosporin A), serve to enhance endocytosis due to their inherent lipophilicity. In such cases a separate lipid anchor is generally not required.

Endocytosis may also be promoted by attachment of a receptor signal, or ligand, to the polypeptide-compound composition. In receptor-mediated endocytosis, the ligand, attached or complexed to the composition targeted for uptake, is capable of binding to a receptor on the cell surface. Such a ligand may be used to enhance general endocytotic uptake, or to target specific cell types, as discussed further below.

IV. Applications

The polymers of the invention can be used to target delivery of attached compounds to specific cells or locations within the body. The specificity of targeting may be controlled by exploiting the pH differential between the cytosol and extracellular medium, or by the use of targeted cell surface receptors.

A. Treating H. pylori infection

If a target cell exists in an acidic environment, direct entry into the cell is facilitated by the pH differential between the extracellular environment and the cytosol of the cell, without requiring entry via endosomes. Such direct entry is generally much faster than endocytotic entry. Examples of such targeting in low-pH environments are given below.

The very acidic environment of the stomach may be specifically exploited, as in treatment of H. pylori infection, by using a polymer composition effective to partition into a membrane at a pH less than about 4.5. Other compartments in the body, including the endosomal compartments of eukaryotic cells, which have a pH in the range of 4.5–6.5, do not reach this low pH and so fail to convert the polymer composition to a lipophilic state required for passage across their lipid layers.

Although a polypeptide with a higher transition pH, e.g. up to 6.5 or 7.0, would still enter H. pylori cells, it could also enter other cells via endocytosis, with a resulting decrease in selectivity.

In order to penetrate a bacterial cell, a composition must be able to cross the outer membrane (in gram negative bacteria), the cell wall and the inner plasma membrane. The bacterial cell wall generally excludes entry of globular compounds of 2000 Da or more. Studies in support of the invention indicate that the polypeptide compositions described herein, though generally of higher molecular weight than 2000 Da, successfully penetrate H. pylori cells. Because the compositions, at low pH, are primarily linear rods rather than globular, it is postulated that they penetrate the cell wall via a reptation mechanism.

Drugs that have been used to target H. pylori include amoxicillin, bismuth salts, metronidazoline, omeprazole, clarithromycin and tetracyclines. Therapy with a single drug has not always been effective, due to pH effects and/or inadequate concentrations of the drug at the infection site. Triple-drug therapy is therefore frequently recommended, using the combination of a bismuth salt (e.g. bismuth subsalicylate), an anti-infective (e.g. metronidazole), and either tetracycline or amoxicillin. (See e.g. Dixon, O'Connor, Glupczynski.) Because the present method affords more selective targeting against the pathogen, higher doses of drug and/or more cytotoxic drug may be delivered, thus providing greater efficiency of both single- and multiple-drug regimens, and a treatment period shorter than the 3–4 weeks generally required for eradication.

This application is one in which benefits could be gained by maintaining the polypeptide intact after delivery of the compound. Specifically, the intact polypeptide-compound composition is unlikely to be absorbed into the stomach or intestinal wall, thus preventing delivery of the attached compound to non-targeted body sites. As noted above, a polypeptide composed of D-amino acids is not degraded by proteolytic enzymes and thus would be preferred for this purpose. A relatively stable compound-polypeptide linkage, such as an amide, would also be preferred in this instance.

B. Targeting Tumor Cells

Most solid tumor masses contain cells which are hypoxic (oxygen deficient), due to insufficient blood supply. This hypoxia makes such cells more resistant to both radiation and drug therapy (see e.g. Kennedy). Delivery of anticancer drugs can also be impaired by the limited vasculature.

The extracellular environment within such solid tumors has been shown to be more acidic than normal tissue (e.g. Kennedy, Tannock, Vaupel) due to factors such as the production of lactic acid under anaerobic conditions. Measured pH's are typically in the range of 6.0–7.0, or, in general, about 0.3 to 1.0 units less than in the corresponding normal tissue (Vaupel).

The extracellular medium of tumor masses also appear to be of lower pH than the intracellular compartment of the tumor cells themselves (Newell). For example, measurements of pH by $^{31}P$ NMR, which measures primarily the intracellular pH, showed that brain tumors and sarcomas had a higher intracellular pH than the corresponding normal tissues (Vaupel).

In accordance with the present method, hypoxic tumor cells, by virtue of their low pH environment, may be targeted by an antineoplastic drug linked to a polypeptide which is effective to partition into a membrane at the pH present in this extracellular environment. Such drugs include, for example, cis-platin, antimetabolites such as methotrexate and fluorouracil, topoisomerase inhibitors such as doxorubicin, alkylating agents such as cyclophosphamide and chlorambucil, and tubulin-binding plant alkaloids such as vinblastine, vincristine, docetaxel, and paclitaxel (Taxol™).

A polypeptide effective for the targeting of hypoxic cells, as described above, could also undergo pH-dependent transition to its lipophilic form in a late stage endosome, where the pH range is typically about 4.5–6.5. However, direct cell entry is generally much faster than endocytosis. In direct cell entry experiments using suitable pH differentials, transport occurs within a matter of minutes; see, e.g., Example 10. Appreciable endocytotic entry, on the other hand, generally takes many hours. Therefore, endocytotic uptake by non-targeted cells would be minimal relative to direct entry into the targeted cancer cells, driven by the existing pH differential between the extracellular medium and intracellular compartment.

C. Treating/Preventing Tooth Decay

Tooth decay (dental caries) is promoted by the production of acid (acidogenesis) by bacteria in breaking down carbohydrates. Studies of pH in sucrose-induced plaque (Igarashi) showed a minimum pH of 4.6±0.2 in 2-day-old plaque; the pH increased to 5.7 after 21 days. The dominant bacteria were Streptococci (>50% of total) and Actinomyces (>10% of total). In another study, bacteria taken from caries-active sites produced a final pH of 4.2 or less in sugar broth (van Houte).

Antibacterial agents may be targeted to the site of decay or potential decay according to the methods described above, using polypeptides effective to partition into a membrane at a pH in the range of about 4.5 to 6.5, and preferably in the range of about 4.5 to 5.5. Suitable antibacterials that have been used in the treatment of dental caries include chlorhexidine, triclosan (Friedman, Bouwsma), xylitol, antibacterial enzymes, and amine fluorides such as 9-octadecen-1-amine hydrofluoride and 1-hexadecylamine hydrofluoride.

D. Targeting Cell Surface Receptors

Drug delivery via endocytosis may be promoted by linking or complexing the polymer-drug composition to a suitable ligand, or receptor signal. Use of such a ligand can provide cell-targeting versatility because certain receptor signals, such as mannose-6-phosphate, biotin, folic acid, and other water soluble vitamins, afford delivery to many cell types (Ludwig) and thus may be used to promote cell entry in many applications. Others may be used to focus delivery into one or a few specific cell types, as discussed further below. It is generally desirable that the linkage between the polymer-drug composition and the ligand be cleavable, so that after transport the polymer-drug can be released free in the cytosol.

Water-soluble vitamins such as riboflavin, thiamine, nicotinic acid and folic acid can be used to target cell surface receptors. These compounds are believed to be taken into the cell by potocytosis, a variation of endocytosis that is specialized for the uptake of small molecules. In potocytosis, receptors are present in small (approx. 50 nm diameter) pits or vesicles on the cell surface, known as caveolae. These caveolae remain at or near the cell surface, going through cycles of opening and closing. Upon closing, proton pumps within the membrane produce a pH of about 6.0 within the caveola.

When the pH of the caveola becomes sufficiently low, the vitamin, with attached polymer, is released from the receptor (Anderson). The polymer-compound composition then inserts into the lipid membrane, after undergoing a pH-dependent transition into a lipophilic conformation, and thereafter transports into the cytosol, according to the mechanism described herein.

Although this pathway does not typically involve as large a pH differential as the endocytotic pathway, it presents certain advantages. The caveolae do not merge with pre-lysosomes, and thus potential exposure of the composition to degradative enzymes is avoided. Furthermore, the water-soluble vitamin is generally released from the polymer when exposed to low pH within the caveola, allowing free polymer-drug to enter the cytosol.

Cells that may be specifically targeted by receptor signals include liver cells (hepatocytes), whose surfaces contain receptors that specifically recognize galactose-terminal glycoproteins. Many malignant cells overexpress certain receptors, and thus it may be possible to selectively target such cells, as has been reported using folate (Mathias) and epidermal growth factor (Deshpande). D-cycloserine has been reported to facilitate transport through the cytoplasmic membrane of bacteria (Chopra, Rapaport).

E. Transport Across the Blood-Brain Barrier

The blood-brain barrier (BBB), which regulates the exchange of materials between the bloodstream and central nervous system, presents a formidable barrier to drug transport. The endothelial cells of cerebral capillaries contain "tight junctions", circumferential bands around a cell that are in close contact with adjacent cells. These junctions prevent transport between cells, and thus, for effective transport, compounds must pass through the endothelial cells themselves. Studies directed to such transport of peptides show that lipophilicity is probably the most important factor in promoting transport of a peptide across the BBB (Banga).

In general, compounds may be transported across a cell by transcytosis. In the case of polarized endothelial cells (i.e., cells having distinct apical and basolateral membranes) within a capillary, the compound is first taken through the apical membrane in the inner capillary wall into a transcytotic vesicle. Such a vesicle typically attains a pH of about 6.0. The vesicle transfers the compound to the basolateral membrane of the endothelial cell, on the outer capillary wall. The compound is then expelled from the transcytotic vesicle, thereby releasing the compound outside of the cell and the capillary.

In accordance with the present method, transportation of a compound across the blood-brain barrier may be effected by linking the compound to a polypeptide of the present invention which is effective to partition into a membrane at a pH within a selected range, as described below. The composition is preferably further linked to a receptor signal, e.g. hypoxanthine or inosine, effective to bind to a receptor on the surface of a cerebral endothelial cell. After delivery to the cerebral bloodstream, the composition is transported across the capillary wall via transcytosis, as described above.

The composition is then available to be taken up by a brain cell via endocytosis and released into the cell cytosol, according to the mechanisms described herein. In the latter process, the endosome is expected to have a pH of about 5.0.

From the above description, it can be seen that the pH at which the polymer is effective to traverse a cell membrane should be between 5.0 and 6.0, or, more generally, below the pH of the transcytotic vesicle in an endothelial cell and above that of the endocytotic vesicle in the ultimate target cell. If the pH were above 6.0, in this case, the polymer would assume its lipophilic conformation within the transcytotic vesicle and penetrate its membrane, thus entering the endothelial cell instead of the targeted brain cell.

F. Transdermal Delivery

The principal permeability barrier of the skin, the stratum corneum, consists of cornified epithelial cells surrounded by an extracellular lipid matrix. The extracellular lipid matrix, which constitutes the principal route for passage of compounds through the skin, consists of lipids (ceramides, cholesterol, free fatty acids, and cholesteryl sulfate) ordered in multiple sheets of lipid bilayers, with water and other polar compounds dispersed between the polar faces of the stacked bilayers. This structure of multiple alternating polar and nonpolar layers presents a formidable barrier to penetration of both hydrophilic and lipophilic compounds. Each of the multiple lipid bilayers acts as a substantial barrier to passage of hydrophilic compounds, while each of the layers of water and other polar compounds between the polar faces of the stacked lipid bilayers acts as a substantial barrier to passage of lipophilic compounds.

It is known that the stacked bilayers of the extracellular lipid matrix can be disordered by a variety of penetration enhancers, such as Azone (1-dodecyl-azacycloheptan-2-one), unsaturated long-chain alcohols, and unsaturated long-chain fatty acids, such as oleic and linoleic acid (Aungst et al., 1986; Rehfeld and Elias, 1982; Golden et al., 1986; Goodman and Barry, 1985, 1986).

While treatment of the skin with penetration enhancers affords improved delivery of a variety of relatively amphiphilic drugs, simple and effective transdermal delivery of many lipophilic and hydrophilic compounds is still not readily achieved by methods known in the art.

In accordance with the present invention, a suitable polypeptide is contacted with the surface of the epidermis in its low-pH lipid-soluble form. Because the pH of the skin surface is typically in the range of 5.0–5.5 (see, for example, Yosipovitch, Korting), polypeptides with transition pH's in this range or higher will exist predominantly in their low-pH form on the skin surface. The peptide, in its lipophilic form, is able to diffuse through the lipid layer of the extracellular matrix of the stratum corneum.

Upon contact with the aqueous compartment underlying the stratum corneum, the composition is actively drawn into this compartment by virtue of progressive ionization and solvation of the polypeptide chain at the near-neutral pH of this compartment. Both hydrophilic and lipophilic compounds may be transported. A preferred polypeptide for this application undergoes a reversible pH-dependent transition at a pH between about 5 and 6.5.

The polymer composition of the instant invention is preferably used in concert with one or more suitable penetration enhancers, as described above. Lipophilic acids, such as oleic or linoleic acid, may be added to maintain the polymer in its low-pH lipophilic form during passage across the lipid layer. These fatty acids also serve as penetration enhancers, as noted above.

Example 11 illustrates the use of a representative polymer composition of the invention to enhance transdermal delivery of the antirejection drug, cyclosporin A.

G. Disposition of Polypeptide after Compound Delivery

As noted above, the polypeptides of the invention are likely decomposed by proteasomes after entering the cytosol of the cell, thus freeing the transported drug or other compound. This release of the drug is shown, for example, in FIG. 2.

In some instances, it may be desirable for the polypeptide to remain intact, in which case it should be synthesized from D-amino acids. One example is in delivery to the stomach, as described for the eradication of *H. pylori,* above. Another is in the selective delivery of highly toxic drugs, e.g. to tumor cells. Because the transporting action of the polypeptide is unidirectional, proceeding from lower to higher pH, the polypeptide attached to the drug prevents the drug from diffusing back out of the target cell to which it was first delivered. Undesirable side effects, resulting from access to non-targeted cells, are therefore minimized.

The intact polypeptide may also prevent or minimize exportation of the delivered drug by cellular processes. Many cells express a glycoprotein which serves as a drug-efflux pump, transporting drug compounds out of the cell. The attached polypeptide will likely interfere with this process and reduce or prevent exportation of the attached drug.

As an alternative to maintaining the entire polypeptide attached to the drug, the polypeptide may be prepared with one or more D-amino acids adjacent to the drug, and the remainder L-amino acids. The L-amino acids will be removed by proteasomes, leaving a shortened polypeptide "tail" of D-amino acids attached to the drug.

It should be noted, however, that when D- and L-amino acid segments are joined, a local disruption of the $\alpha$-helix is likely to arise at the junction of such segments. In this case, hydrogen bonding and shielding of free carboxyls in the vicinity may be less efficient, and the a-helical form of the polypeptide less lipophilic, than if all one configuration were used.

H. Formulation and Administration

Formulations containing the compositions of the invention may be in solid, semi-solid, or liquid dosage forms, such as, for example, tablets, capsules, powders, sustained-release formulations, solutions, suspensions, emulsions, suppositories, ointments, lotions, or aerosols, preferably in unit dosage forms suitable for simple administration of precise dosages.

Such formulations typically include a conventional pharmaceutical carrier or excipient and may additionally include other medicinal agents, carriers, or adjuvants. Preferably, the formulation will contain about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary compounds such as wetting agents, emulsifying agents, or buffers.

Liquid compositions can be prepared by dissolving or dispersing the polypeptide-compound composition (about 0.5% to about 20%), and optional pharmaceutical adjuvants, in a carrier, such as, for example, aqueous saline, aqueous dextrose, glycerol, or ethanol, to form a solution or suspension.

The composition may be administered to a subject by a variety of known routes, e.g., orally, transdermally, as described above, or parenterally, e.g., by intravenous, subcutaneous, intraperitoneal, or intramuscular injection.

For use in oral liquid preparation, the composition may be prepared as a solution, suspension, emulsion, or syrup, being supplied either in liquid form or a dried form suitable for hydration in water or normal saline.

Transdermal delivery typically involves the use of a transdermal "patch" which allows for slow delivery of compound to a selected skin region. Examples of transdermal patch delivery systems are provided by U.S. Pat. No. 4,655,766 (fluid-imbibing osmotically driven system), and U.S. Pat. No. 5,004,610 (rate controlled transdermal delivery system).

For transdermal delivery, it may be desirable to include permeation enhancing compounds, as described in above. Such formulations may be provided as occluded dressings to the region of interest, or may be provided in one or more of the transdermal patch configurations described above.

For parenteral administration, an injectable composition for parenteral administration will typically contain the composition of the invention in a suitable IV solution, such as sterile physiological salt solution. The composition may also be formulated as a suspension in a lipid or phospholipid, in a liposomal suspension, or in an aqueous emulsion.

Methods for preparing such dosage forms are known or will be apparent to those skilled in the art; for example, see *Remington's Pharmaceutical Sciences* (1980).

The following examples illustrate but in no way are intended to limit the present invention.

EXAMPLE 1

Representative Methods for Preparation of the Polymer Composition

A. Assembly

A synthesis resin is prepared so that β-alanine will comprise the C-terminal residue of the polypeptide, as illustrated in FIG. 10. One gram of crosslinked polystyrene resin containing 0.7 mMol p-alkoxybenzyl alcohol, 1 (Cat. # A3039, Sigma Chem. Co., St. Louis, Mo.) is dissolved in 8 ml of N-methylpyrrolidinone (NMP), and 0.62 g of fluorenylmethoxycarbonyl (FMOC) β-alanine 2 is added, followed by 316 μl of N,N'-diisopropyl carbodiimide and 41 μl N-methylimidazole. This slurry is incubated with agitation at 37° C. for 100 minutes, then washed thoroughly with NMP, followed by $CH_2Cl_2$, drained, and dried. This affords a resin 3 with a loading of about 250 μmole β-alanine-FMOC per gram of material. Subsequent addition of protected/activated amino acids to extend the polypeptide can be carried out as per Atherton et al. (1988). This method uses N-fluorenylmethoxycarbonyl pentafluorophenyl amino acid esters, as shown at 4. If desired, an end modifying structure may be added, as shown in FIGS. 8B–C, where an activated ester 5 is reacted with the N-terminus of the polypeptide. The polypeptide is then cleaved and deprotected according to standard methods.

When it is desired to attach the compound to be transported (typically a drug) at one or more positions other than the terminus of the polypeptide, a suitably-protected lysine or cysteine is typically incorporated at the selected attachment position(s). Following cleavage of the completed polypeptide from the synthesis resin and sidechain deprotection, the drug can be attached to the resultant amine or sulfhydryl moiety, as described in Example 2, to afford linkages illustrated in FIG. 9.

Alternatively, certain drugs may be linked, suitably protected if necessary, to the gamma carboxyl of glutamic acid, or the β-carboxyl of aspartic acid, via an ester linkage. The resultant amino acid is then incorporated into the polypeptide chain at one or more selected positions. Such drugs must have structures which survive the conditions used to assemble the polypeptide, to cleave the polypeptide from the synthesis resin, and to deprotect the side chains.

B. End Modifications

In cases where the compound to be transported is not linked through the N-terminal amine, it is generally desirable to shield or delete at least some of the N-terminal polar sites. This is readily achieved by cleaving the FMOC moiety from the N-terminus of the completed resin-bound polypeptide and then treating with glutaric anhydride, acetic anhydride, or the nitrophenyl ester of the succinamide derivative shown in FIG. 6E, to give terminal structures such as illustrated in FIGS. 6B, 6C, and 6D, respectively.

C. Cleavage from the Synthesis Resin, Deprotection and Isolation

The completed polypeptide can be cleaved from the resin by washing the resin with $CH_2Cl_2$, draining, and adding, per gram of resin, a solution comprising 10 ml trifluoroacetic acid (TFA), 10 ml $CH_2Cl_2$, and 400 mg dithioerythritol. After 20 minutes the cleavage solution is drained into a flask and the $CH_2Cl_2$ removed by evaporation. Thereafter, 5 to 10 ml TFA is added and the solution held at 43° C. for 4 hrs to effect removal of protective groups. Workup of the deprotected polypeptide generally entails ether precipitation, thorough washing of the precipitate with ether, and drying.

It should be appreciated that there are a variety of other peptide assembly methods known in the art which are also suitable for preparing the composition of the invention.

EXAMPLE 2

Attaching Compounds to Polypeptide on Column

For drugs or other compounds (e.g., a fluorescent tag for partitioning and cell entry studies) which can survive the conditions used to cleave the polypeptide from the synthesis resin and deprotect the sidechains, it is often desirable to cleave the FMOC from the N-terminus of the completed resin-bound polypeptide and then link such compound to the terminal amine. In such cases the compound to be attached is typically activated, by methods known in the art, to produce an active ester or active carbonate moiety effective to form an amide or carbamate linkage, respectively, to the polypeptide, such as illustrated in FIG. 9.

Examples 3–7, following, describe representative methods for attaching compounds to polypeptides after removal from the column.

EXAMPLE 3

Disulfide Linkage to Cysteine Residue of Polypeptide

In a convenient and well established method for linking a drug to a cysteine of the polypeptide composition, the deprotected polypeptide is reacted with 2,2'-dipyridyl disulfide, and the drug containing a sulfhydryl moiety is added to form the desired disulfide link, as illustrated in FIGS. 7A and 11. A particular advantage of such a disulfide linkage is that it is relatively stable in the extracellular compartment and within endosomes, but after transport across the endosomal membrane it is readily cleaved in the cytosolic compartment. The following specific examples illustrate applications of this method.

3A. Preparation of a disulfide-linked Polypeptide-cyclosporin conjugate. A polypeptide with the sequence (FMOC-ELLD-[LELLD]$_7$LELLβ; β=β-alanine) is assembled on the solid phase support by the methods given in Example 1A. The terminal FMOC group is cleaved by treatment with 20% piperidine in NMP and a terminal S-tritylated FMOC-cysteine is introduced by the method of Example 1A. Following cleavage of the FMOC group and acetylation, the polypeptide is cleaved from the column, deprotected, precipitated, and washed as per Example 1C. The polypeptide is dissolved in pH=7.5 tris buffer containing 0.1 M dithiothreitol. The solution is diluted with an equal volume of acetonitrile and treated with sufficient dipyridyl disulfide to create a 0.4 molar solution. After stirring for 2 hours at room temperature, the mixture is diluted with an equal volume of water and washed with sufficient water-saturated ethyl acetate to remove excess dipyridyl disulfide. The solution is partially evaporated to remove residual ethyl acetate and the product isolated by passage of the solution through Amberchrome (TosoHaas) followed by elution with 0–80% acetonitrile with a 0.01% triethylamine buffer followed by lyophilization.

In a separate flask, cyclosporin A metabolite 17, which has a primary hydroxyl group (Eberle and Nuninger, 1992), is treated with succinic anhydride using the method of Chen and Tai (1995), and the acid is converted to the activated ester with N-hydroxysuccinimide and 1-(3-dimethylaminopropyl)-3-ethylcarbodiimide methiodide (Aldrich). The product is dissolved in DMF and treated with 2-aminoethanethiol hydrochloride and triethylamine. The reaction mixture is diluted with dichloromethane and washed with 0.1M citric acid to remove excess reagents. The product is obtained by evaporation. The residue is dissolved in DMF and treated with the pyridyl polypeptide disulfide from the previous paragraph.

The product is isolated by evaporative removal of the DMF followed by reverse phase purification on Amberchrome eluting with 0–80% acetonitrile in a 0.01% triethylamine buffer followed by lyophilization. Alternatively, following evaporation of the DMF, the product is dissolved in 0.1M Na$_2$HPO$_4$ and washed well with water-saturated ethyl acetate. After partial evaporation to remove the dissolved ethyl acetate, formic acid is added to precipitate the product, which is washed well with water containing 0.1% formic acid, then dried thoroughly under high vacuum.

3B. Preparation of a disulfide-linked polypeptide-Taxol™ conjugate. A polypeptide with the sequence (AcNH-CELLD-[LELLD]$_7$LELLβ; β=β-alanine) with a terminal pyridyl disulfide moiety on the cysteine is prepared as in the previous section.

In a separate vessel, Taxol™ is converted into 7-glutaryl Taxol™ by the method of Gueritte-Vogelein et al. (1991). The carboxyl group of this species is activated as the N-hydroxysuccinimde ester with N-hydroxysuccinimde using 1-(3-dimethylaminopropyl)-3-ethylcarbodiimide methiodide (Aldrich) and 4-dimethylaminopyridine in dichloromethane. The product is dissolved in DMF and treated with 2-aminoethanethiol hydrochloride and triethylamine. The reaction mixture is diluted with dichloromethane and washed with 0.1M citric acid to remove excess reagents. The product is obtained by evaporation. The residue is dissolved in DMF and treated with the pyridyl polypeptide disulfide from above. The product is isolated as per the cyclosporin example.

EXAMPLE 4

Thioether Linkage to Cysteine Residue of Polypeptide

4A. Preparation of a thioether-linked polypeptide-cyclosporin conjugate. Cyclosporin A metabolite 17 (see Example 3A) is treated with chloroacetic anhydride in 1:1 dichloromethane/pyridine to form an acid chloride (see FIG. 11). The excess reagent is quenched by the addition of water, and the solvent is evaporated. The residue is dissolved in ethyl acetate and washed with 0.1M citric acid, 0.1M sodium bicarbonate, and brine, then evaporated. The residue is redissolved in DMF.

The polypeptide pyridyl disulfide prepared in Example 3A is dissolved in pH 9.0 borate buffer. This is mixed with an equal volume of the above DMF solution (ratio of CS:polypeptide=4:1), and TCEP (tris(carboxyethyl) phosphine hydrochloride) is added. After stirring at room temperature, the product is isolated as in Example 3A.

4B. Preparation of a thioether-linked polypeptide-Taxol™ conjugate. A polypeptide with the sequence (FMOC-ELLD-[LELLD]$_7$LELLβ; β=β-alanine) is prepared on a solid support as in example 1A. The terminal FMOC group is removed and the column treated with acryloyl chloride in dichloromethane containing diisopropylethylamine, to form a terminal acrylyl group (FIG. 11). The polymer is removed from the column, deprotected using trifluroacetic acid according to standard methods, precipitated and washed. The product is dissolved in pH 9.0 borate buffer.

In a separate flask, Taxol™ is converted into a thiolated species by the methods in Example 3A. The product is dissolved in DMF, mixed with the acrylamide species from the paragraph above, and TCEP is added. After stirring at room temperature, the product is isolated as in Example 3A.

EXAMPLE 5

Carbamate Linkage to Amine Moiety of Polypeptide

The ether precipitate of a deprotected polypeptide containing one or more amine moieties, prepared as in example 1C, is dissolved in aqueous 0.1 M Na$_2$HPO$_4$. Formic acid is added sufficient to precipitate the polypeptide, and the precipitate is collected by centrifugation and washed twice with 0.1% formic acid in water. The polypeptide precipitate is then dried under high vacuum overnight.

The compound to be linked to the polypeptide, containing at least one hydroxyl moiety, is activated by reacting with 3 equivalents of bis-nitrophenyl carbonate and 0.1 equivalent of triethylamine in NMP. After activation, the excess bis-nitrophenyl carbonate is removed and the active carbonate product (see FIG. 11) then reacted with 0.5 to 2 equivalent of the polypeptide composition, prepared as described above, in NMP. Good coupling is generally achieved by incubation for 12 to 72 hours at 43° C.

EXAMPLE 6

Amide Linkage to Amine Moiety

6A. Preparation of an amide-linked polypeptide-cyclosporin conjugate.

1. Using a defined length peptide. A polypeptide with the sequence (FMOC-ELLD- [LELLD]$_7$LELLβ; β=β-alanine) is assembled on the solid phase support by the methods given in example 1A. The terminal FMOC group is cleaved as per the method in example 1A and the resin treated with an excess of the bis-(4-nitrophenyl) ester of glutaric acid in NMP. (The ester is prepared from glutaryl chloride and nitrophenol using triethylamine in dichloromethane. Following washing with sodium hydroxide solution to remove excess nitrophenol and unreacted glutaric acid species, the evaporated product is recrystallized from toluene.) The activated polypeptide is cleaved from the column, precipitated, and washed using the method in example 1C.

In a separate flask, cyclosporin A metabolite 17 (see Example 3A) is treated with the FMOC derivative of glycine and 1-(3-dimethylaminopropyl)-3-ethylcarbodiimide methiodide (Aldrich) in dichloromethane in the presence of 4-dimethylaminopyridine catalyst. The reaction mixture is washed with acid and base to remove excess reagents and the product chromatographed on silica gel using 0–2% methanol in chloroform. Removal of the FMOC group is accomplished by treatment of the FMOC-glycyl cyclosporin with 20% triethylamine in DMF at 50 degrees C. for one hour. The triethylamine is removed by evaporation under vacuum and the free amino derivative mixed with the activated polypeptide above. The solution is evaporated in vacuo to a minimum volume and allowed to sit at 42 degrees for 24 hours. The product is isolated as in Example 3A.

2. Using a Random Length High Glutamic Acid Content Peptide. A high glutamic acid content, random length peptide with C-terminal initiator region, is prepared as follows.

Chlorotrityl resin preloaded with N-Fmoc-β-alanine (Novabiochem, LaJolla Calif.) is reacted with N-α-Fmoc-L-glutamic acid γ-t-butyl ester and N-α-Fmoc-L-leucine using HBTU (Novabiochem) and diisopropylethylamine to produce FMOC-LeuGlu(OtBu)LeuLeu-NHCH$_2$CH$_2$COO-Resin. The Fmoc group is then removed in the usual manner.

The resin bound initiator peptide is treated six times with the carboxyanhydride of L-glutamic acid γ-(4-methoxy benzyl) ester (Hanabusa et al., 1984) in DMF, using an anhydride to initiator ratio of about 10 to 1, which is sufficient to add about 40–50 protected glutamic acid residues to the peptide. The N-terminus is then reacted with excess bis-(p-nitrophenyl) ester of glutaric acid.

The peptide is cleaved from the resin and deprotected as described in Example 1C. The residue after evaporation is dissolved in dichloromethane and washed with water to remove traces of trifluoroacetic acid. The isolated polyacid is dissolved in DMF and treated with Taxol™-7-alanine (Mathew et al., 1992). The reaction mixture is diluted with pH 7.0 phosphate buffer and the product purified by ion exchange chromatography on Q-Sepharose (Pharmacia, Piscataway, N.J.) using a 0–1.0 M NaCl gradient. The material is then isolated as the sodium salt by adsorption to an Amberchrome SD (TosoHaas), elution with a 0–80% acetonitrile gradient, and lyophilization.

6B. Preparation of an amide-linked polypeptide-Taxol™ conjugate. A polypeptide with the sequence (H$_2$N-ELLD-[LELLD]$_7$LELLβ; β=β-alanine) is prepared as in Examples 1 and 5 with a terminal amino group.

In a separate vessel, Taxol™ is converted into 7-glutaryl Taxol™ by the method of Gueritte-Vogelein et al. (1991). The carboxyl group of this species is activated as the N-hydroxysuccinimde ester with N-hydroxysuccinimde using 1-(3-dimethylaminopropyl)-3-ethylcarbodiimide methiodide (Aldrich) and 4-dimethylaminopyridine in dichloromethane. After washing to remove excess reagents and byproducts, the ester is isolated by evaporation and mixed with the polypeptide in DMF. The solution is evaporated in vacuo to a minimum volume and allowed to sit at 42 degrees for 24 hours. The product is isolated as in Example 3.

6C. Preparation of an amide linkage between a polypeptide and the 5' terminus of a 20-mer Morpholino antisense oligo. Structures and subunit sequences of the Morpholino oligo and polypeptide are as follows, with reference to FIG. 13:

R$_1$ = -
   ELLDLELLDLELLDLELLDLELLDLELL-
   DLELLDLELLDLELLβ where D=aspartic acid, E=glutamic acid, L=leucine, β=β-alanine

R$_2$ = 5'-
   G*G*UG*G*UUC*C*UUC*UC*A*G*UC*G*G*-
   acetyl where

A*=Morpholino 6-benzoyladenine

C*=Morpholino 6-benzoylcytosine

G*=Morpholino 6-phenylacetylguanine

U=Morpholino uracil

Figure 13A:
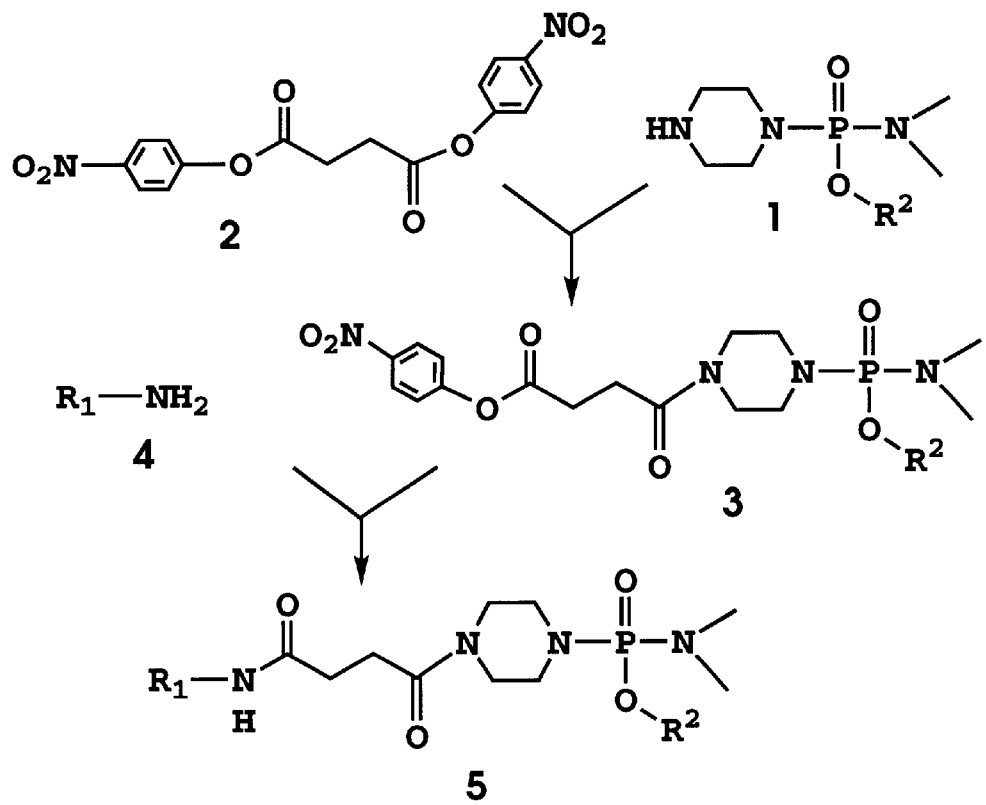
FIGS. 13A–C show procedures for linking a polypeptide of the invention to a Morpholino antisense oligomer.
Figure 13B:
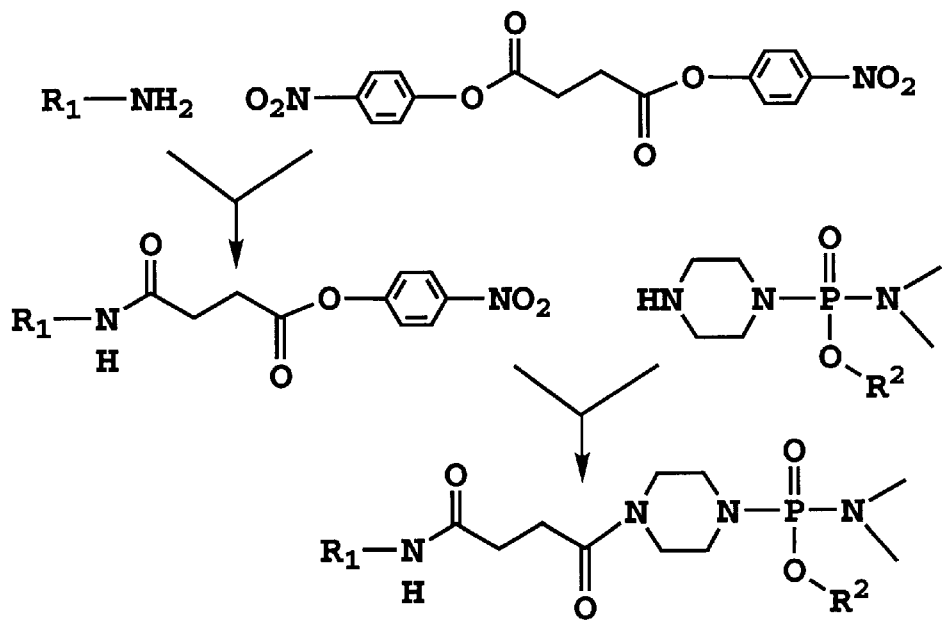

Procedure 1 (FIG. 13A): 17 mg (2 µMole) of base-protected Morpholino antisense oligo (MW 8361), shown in FIG. 13A at 1, prepared as per Summerton & Weller (1993), is suspended in 200 µl NMP. Bis(p-nitrophenyl) succinate 2 (7.2 mg; 20 µMol) is added, and the preparation is incubated for 4 hours at 43° C. The unreacted succinate is removed by precipitating the Morpholino-succinate product from 30 ml of acetonitrile, centrifuging, discarding the supernatant, resuspending the pellet in 0.4 ml of NMP, adding to 30 ml of acetonitrile, centrifuging, discarding the supernatant, and drying the pelleted Morpholino-succinate product 3 under high vacuum.

The Morpholino antisense oligo with succinate linker 3 (2 µMole), prepared above, is placed in a 0.75 ml vial containing a 3 mm magnetic stir bar with 31 mg (6 µMole) of the deprotected 44-amino acid polypeptide R$_1$-NH$_2$, as defined above, shown at 4, precipitated from aqueous solution as described in Example 2B(iii), having a free amine moiety on the N-terminus. DMF (150 µL) is added and the mixture stirred in a warm water bath till dissolution is complete. The reaction mixture is then incubated at 43° C. for 72 hours, diluted with 200 µL NMP, and transferred to a 2 ml screw cap vial. 600 µL of conc. NH$_4$OH is added and the solution incubated 18 hours at 43° C. to deprotect the purine and pyrimidine bases of the Morpholino antisense oligo. The product 5 is purified as described in Example 8C.

Procedure 2 (FIG. 13B): In this procedure, the activated succinate linker is added to the polypeptide, and the adduct is reacted with the Morpholino antisense oligo. Accordingly, an NMP suspension of 180 mg of synthesis resin/polypeptide, prepared as in Example 1, is treated with 20% piperidine in NMP, then washed repeatedly with NMP. Bis(p-nitrophenyl) succinate (150 mg) is dissolved in 0.9 ml NMP, added to a short fritted column containing the resin/polypeptide preparation and incubated 2 hours at 43° C. Excess succinate linker is washed out and the product cleaved from the synthesis resin, as described in Example 1C, to give a polypeptide-succinate product (MW 5329).

Into a 0.75 ml vial with a magnetic stir bar are placed 32 mg (6 µMole) of the polypeptide-succinate product prepared above and 17 mg (2 µMole) Morpholino antisense oligo (1), containing a 5' secondary amine moiety, and 150 µL DMF is added. The mixture is stirred in a warm water bath till dissolution is complete. The reaction mixture is then incubated at 43° C. for 48 hours. Thereafter, the reaction mixture is diluted with 200 µL NMP and transferred to a 2 ml screw cap vial. 600 µL of con NH$_4$OH is added and the solution incubated 18 hours at 43° C. to deprotect the purine and pyrimidine bases of the Morpholino antisense oligo. The product (5) is purified as described in Example 8C.

Procedure 3 (FIG. 13C): Morpholino antisense oligo is prepared wherein the first subunit, containing a 5'-SH, is linked to the synthesis resin via a disulfide bond, according to methods known in the art. The Morpholino oligo, with bases still protected, is cleaved from the synthesis resin using N-methyl pyrrolidinone containing 1% wt/vol dithiothreitol and 5% v/v triethylamine. The eluted oligo is precipitated with t-butylmethyl ether and the pellet washed twice with t-butylmethyl ether and then dried under high vacuum to give base-protected Morpholino oligo with 5'-SH and a 3'acetyl.

Polypeptide still on the synthesis resin, prepared as illustrated in FIG. 10, having the sequence $E_{32}MELML\beta$ (N-terminus to C-terminus), is capped on the N-terminus using chloroacetic anhydride in dichloromethane, and the resin is washed thoroughly. The polypeptide is then cleaved and eluted from the resin with 49:49:2 $TFA:CH_2Cl_2:H_2O$, the $CH_2Cl_2$ is removed under aspirator vacuum, 98:2 $TFA:H_2O$ is added, and the solution is incubated from 4 hours at 43° C. The polypeptide is then precipitated with t-butylmethyl ether and the pellet washed twice with t-butylmethyl ether and dried under high vacuum to give the chloroacetylated polypeptide shown in FIG. 13C.

Figure 13C:
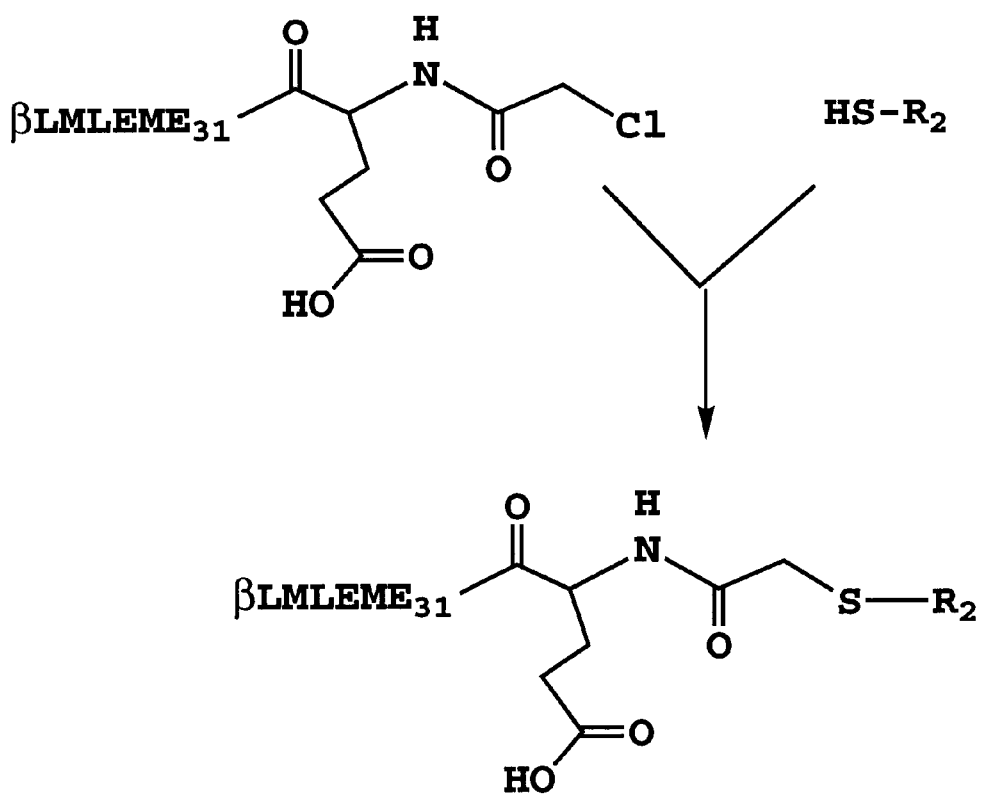
Figure 14A:
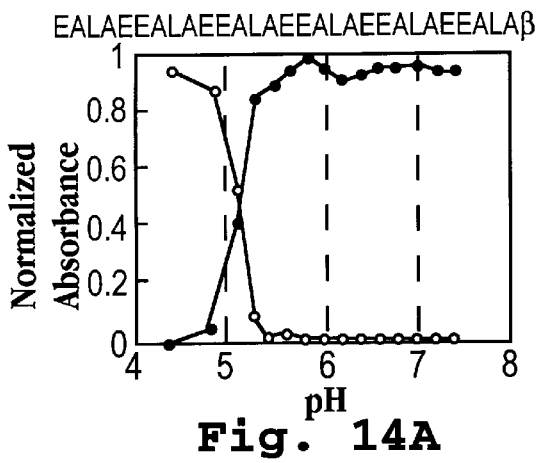
FIGS. 14A–14F show octanol/water partitioning properties of several exemplary polypeptides, as a function of pH.
Figure 14D:
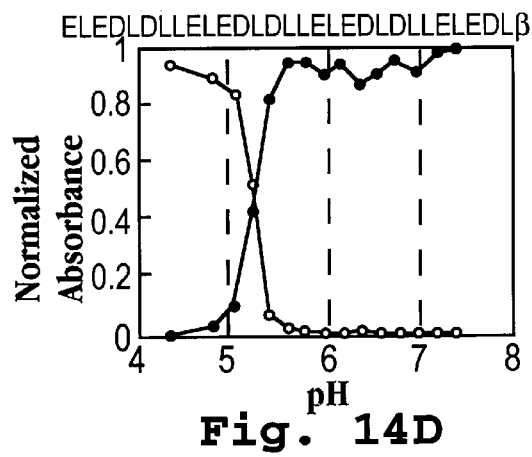
Figure 14B:
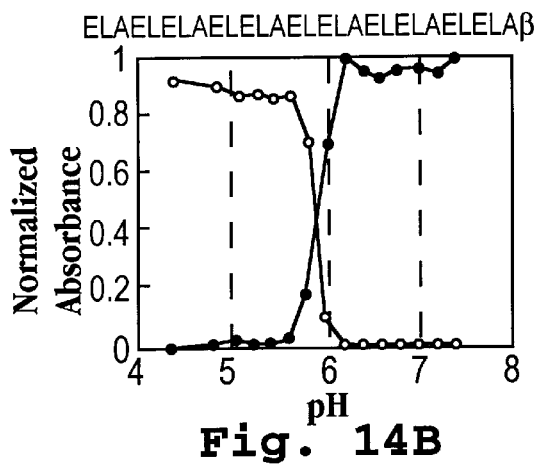
Figure 14E:
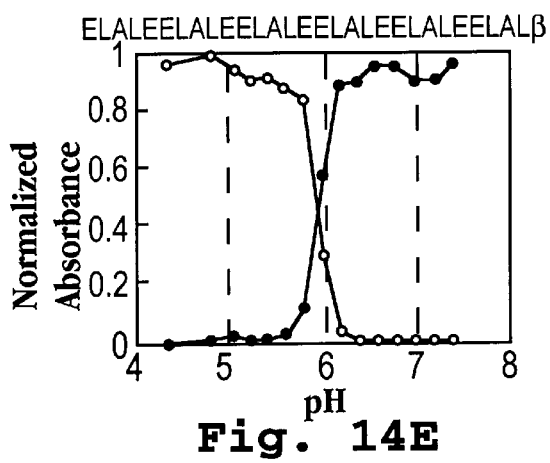
Figure 14C:
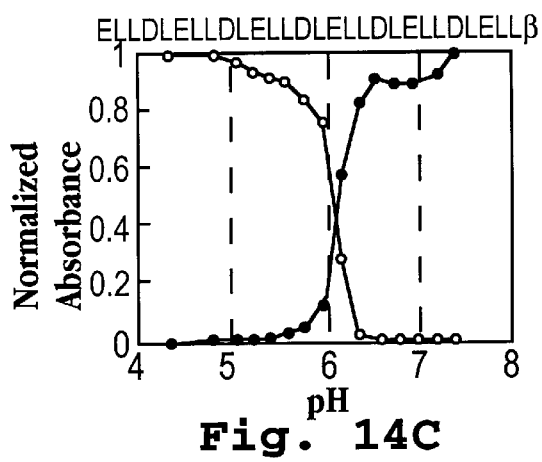
Figure 14F:
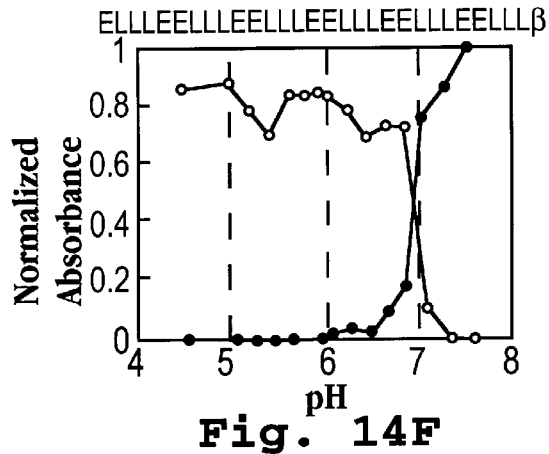

The Morpholino oligo and polypeptide are coupled by adding 5 µmole 5'-SH Morpholino oligo, 10 µmole chloroacetyl polypeptide, and 400 µmole N,N-dimethyl ethanolamine to 1 ml formamide, stirring until dissolution is complete, and then incubating at room temperature for 2 hours to give polypeptide-Morpholino oligo joined by a thioether link, as shown in FIG. 13C. The bases of the Morpholino oligo are deprotected by adding two volumes of concentration $NH_4OH$ to the reaction mixture and incubating 16 hours at 43° C. After releasing excess $NH_3$ the product is purified by anion exchange chromatography, as described in Example 8C.

EXAMPLE 7A

Amide Linkage to Carboxyl Moiety

This example describes the preparation of an amide-linked polypeptide-Taxol™ conjugate with a random length, high glutamic acid content peptide.

A high glutamic acid content, random length peptide with C-terminal initiator region, is first prepared as follows.

Chlorotrityl resin preloaded with N-Fmoc-β-alanine (Novabiochem) is reacted with N-α-Fmoc-L-glutamic acid γ-t-butyl ester and N-α-Fmoc-L-leucine using HBTU (Novabiochem) and diisopropylethylamide to produce Fmoc-Leu-Glu (OtBu) LeuLeu-NHCH$_2$CH$_2$COO-Resin. The protected peptide is removed from the resin by treatment with 0.5% trifluoroacetic acid in dichloromethane. The residue is redissolved in dichloromethane and treated with diphenyldiazomethane (Kametani et al.) to produce the C-terminal diphenylmethyl ester, and the product is precipitated with hexane. The residue is dissolved in dichloromethane and the product precipitated with ether/hexane. The precipitate is dissolved in DMF containing 20% (v/v) piperidine. The solution is evaporated and the amino terminated initiator peptide is ready for elongation.

The initiator peptide is dissolved in DMF and reacted with the carboxyanhydride of L-glutamic acid γ-(4-methoxy benzyl) ester (Hanabusa et al.). The ratio of anhydride to initiator was about 60 to 1, which is sufficient to add about 40–50 protected glutamic acid residues to the peptide. The reaction was quenched by the addition of acetic anhydride, the solvent removed by evaporation, and the product purified by repetitive precipitations from dichloromethane using ether/hexane.

The peptide is deprotected as described in Example 1C, and prepared for conjugation by dissolution in 0.1 M $Na_2HPO_4$ followed by precipitation with formic acid, as described in Example 5. The polyacid is dissolved in DMF and treated with Taxol™-7-alanine (Mathew et al.) and 1-(3-dimethylaminopropyl)-3-ethylcarbodiimide methiodide, sufficient to substitute 5–30% of the acid side chains. The reaction mixture is diluted with pH 7.0 phosphate buffer and the product purified by ion exchange chromatography on Q-Sepharose (Pharmacia) using a 0–1.0M NaCl gradient. The material is then isolated as the sodium salt by adsorption to an Anberchrome SD (TosoHaas), elution with a 0–80% acetonitrile gradient, and lyophilization.

EXAMPLE 7B

Amide Linkage to N-terminal Cysteine

Very efficient coupling can be carried out between a drug or other compound containing an active thioester and an N-terminal cysteine residue, according to the method of Dawson et al. (1994). As indicated in FIG. 11, this coupling proceeds in two steps. Attack of the cysteine sulfhydryl on the initial thioester is followed by a rapid intramolecular attack by the N-terminal amine on the product thioester to form an amide linkage.

EXAMPLE 8

Representative Methods for Purification and Structural Analysis of Polymer-Compound Products A. Silica Gel Chromatography For many polypeptide-drug products, where the polypeptide component dominates the chromatographic properties of the composition, purification is readily achieved by silica gel chromatography. A mixture of isopropanol and 25% aqueous trimethylamine, in proportions ranging from about 1:1 to 3:1, v/v, typically provides good chromatographic resolution.

B. Purification by Partitioning

Polypeptide compositions which partition well into octanol at reduced pH (generally those having less than 50% acid amino acid composition) can often be effectively separated from undesired failure sequences generated during polypeptide assembly by partitioning between n-octanol and an aqueous buffer having a pH about 0.2 pH units below the transition pH of the polypeptide. The purified polypeptide can be recovered from the octanol phase by partitioning into aqueous $Na_2HPO_4$ and then precipitating with formic acid. Typically this purification procedure is carried out before attachment of the drug. This "purification-by-function" method has been found useful for preparations of quite long polypeptides containing a significant fraction of failure sequences.

C. Ion Exchange/Reverse Phase Chromatographies

A particularly versatile method for purifying polypeptide-drug products employs ion exchange chromatography followed by reverse phase chromatography, where the latter stage removes salt and provides additional purification. Use of this purification method is described for the polypeptide-Morpholino antisense oligo products whose syntheses are described in Example 6C and whose structures are shown in FIG. 13.

Polypeptide-Morpholino oligo preparation is transferred to a rotovap flask, and excess ammonia is removed under aspirator vacuum. Approx. 10 ml of Tris acetate buffer (0.1 M Trizma base, acetic acid to pH 8) is added, and the solution is loaded onto a 2.5 cm by 15 cm column of Macro Prep Q anion exchange resin (BioRad Corp.). After loading, the column is washed (flow rate 5 ml/min) for 10 min. with Tris acetate buffer, followed by elution with Tris acetate buffer, increased linearly from 0 to 1.0 M in NaCl, over 40 min. In this system, the Morpholino antisense oligo (monitored at 254 nm) elutes in the first 15 minutes, and the polypeptide-Morpholino product elutes at about 30 minutes.

The polypeptide-Morpholino peak is collected and then desalted on a 2.5 cm by 15 cm column of 50 μm polypropylene (Polysciences Corp.). This reverse phase column is washed for 15 min. with 1% con $NH_4OH$ and then eluted with a 0 to 80% acetonitrile gradient, 1% in conc. $NH_4OH$, over 40 minutes at a flow rate of 5 ml/min. Fractions containing the polypeptide-Morpholino oligo product are combined, rotovaped briefly to remove acetonitrile and ammonia, and then freeze dried.

D. Mass Spectral Analysis

For mass spectral analysis, a portion of the polypeptide-Morpholino product is suspended at a concentration of 20 μM in 1% conc. $NH_4OH$. This material, co-crystallized with 3,4,5-trihydroxyacetophenone/diammonium citrate (1:2), is analyzed by laser-desorption time-of-flight mass spectroscopy. In a representative analysis a mass of 11,881 was found, which is in close agreement with the calculated mass of 11,861 expected for the polypeptide-Morpholino product shown in FIG. 13.

EXAMPLE 9

Assessment of Partitioning Properties

In optimization of a polypeptide composition for a particular delivery application, it is often desirable to first carry out partitioning studies on the polypeptide component alone. In such studies it is generally useful to add a chromophore or fluorophore tag to simplify quantitation of the polypeptide's distribution between the octanol and aqueous phases. In this regard, 5-carboxy fluorescein constitutes a tag which is easily quantitated and which does not have an undue impact on the partitioning properties of polypeptides of reasonable length. This tag has the added advantage of providing an easily visualized signal suitable for cell entry studies.

A representative partitioning study is described below. Stock buffer 1 {0.1 M citric acid ($pK_{a1}$=3.14; $PK_{a2}$=4.77; $PK_{a3}$=6.39), 0.1M N-morpholineethanesulfonic acid (MES; $PK_a$=6. 1) and 0.1 M phosphoric acid ($pK_{a1}$=2.2; $pK_{a2}$=7.2)} and stock buffer 2 (0.1 M MES sodium salt, 0.1 M trisodium citrate, and 0.1 M disodium phosphate) are prepared. Stock buffer 1 is titrated with stock buffer 2 to form a series of buffers ranging from pH 4 to pH 8 in increments of about 0.2 pH units.

A set of 0.75 glass ml vials, where each vial contains 0.28 ml of one buffer of the set plus 0.3 ml of solvent, is prepared. The solvent is n-octanol for polypeptides containing less than about 50% acid amino acids and n-pentanol for polypeptides containing more than about 50% acid amino acid. To each vial of this set is added 20 μl of a 0.1 mM aqueous solution of polypeptide having an attached carboxy fluorescein. Each of these vials is capped, shaken thoroughly, and then centrifuged to separate the phases. Thereafter, 150 μl of the upper octanol phase is added to 150 μl of 85% isopropanol/15% 1,8-diazabicyclo [5.4.0]undec-7-ene (DBU), and the absorbance of this solution is measured at 500 nm. Next, 150 μl of the lower aqueous phase is added to 150 μl of 85% isopropanol/15% DBU, and the absorbance is measured.

FIGS. 14A–F show plots of these absorbance values as a function of pH for six representative fluorescein-tagged polypeptide compositions of the invention, where the six different polypeptides exhibit octanol/water transition pH values ranging from 5.1 to 6.9.

EXAMPLE 10

Assessment of Cytosolic Entry

A. Direct Entry

This Example describes a useful method for testing for transport of a fluorescein-tagged polypeptide composition, with or without attached drug, from the extracellular medium directly into the cytosol of adherent animal cells. It should be noted that appreciable cell entry via endocytosis does not occur in the short time period (about 20 minutes) of this procedure. Because mounting medium, which is generally used in fluorescence microscopy, modifies both the osmolarity and the pH of the cells' environment, it is recommended that mounting medium not be used in these cell entry studies. Instead, cells are viewed using a water-immersion objective. Further, it is desirable that the culture medium in which the cells are viewed does not contain phenol red, which is typically used as a pH indicator in culture medium, because this compound interferes with the fluorescent signal.

The procedure for a direct-cell-entry study is described below. Medium 1 comprises serum-free medium buffered with 20 mM MES (morpholine ethane sulfonic acid) adjusted to pH 6.5 with NaOH. Medium 2 comprises serum-free medium buffered with 50 mM MES adjusted to pH 5.0.

A 150 μl aliquot of a 1 mM solution of fluorescein-tagged polypeptide composition is diluted into 1.9 ml of Medium 1, and 0.5 ml portions are added to 2 cm×2 cm wells in four glass chambered slides in which Hela cells were plated 24 hours earlier. After 10 minutes 375 μl of Medium 2 is added to wells 2, 3, and 4 (giving pH 6.0). After a further 10 minutes an additional 375 μl of Medium 2 is added to wells 3 and 4 (giving pH 5.8). Ten minutes later, a further 500 μl of Medium 2 is added to well 4 (giving pH 5.6). After each addition the slides are swirled gently to thoroughly mix the solutions. Ten minutes after the last addition, all wells are aspirated and each well washed with three 1 ml volumes of DME-F12 culture medium plus 10% FBS, pH 7.4, and the cells are observed via fluorescence microscopy.

Cytosolic entry is generally evidenced by a diffuse fluorescence throughout the interior of the cells. However, it should be noted that some compounds (e.g., antisense oligomers) subsequently pass from the cytosol to the nucleus, where they preferentially accumulate. Thus, nuclear accumulation in direct entry experiments is also evidence for successful cytosolic entry.

In addition to the above-described qualitative assessment of cytosolic entry by fluorescence microscopy, it should be appreciated that qualitative and/or quantitative functional assays specific for the drug being transported can also be carried out following treatment of the cells in reduced-pH medium.

The above procedure provides information on how low the pH must be in order to effect transmembrane transport of a given polypeptide composition of the invention, including, when desired, the attached compound to be transported.

It should be noted that superior entry was generally obtained when the polymers were neutralized during purification with triethylamine, rather than with an alkali metal base or ammonia. This effect may have been due to the relatively lipophilic counterion. Accordingly, polypeptides to be tested should be purified in a consistent manner to minimize any such effect of the counterion on the test results.

B. Entry Via Endocytosis

When a fluorescent-tagged polypeptide is endocytosed into cells, observation of a perinuclear punctate pattern is indicative that the tagged material is localized in the endosomal/lysosomal compartment. However, a diffuse fluorescence throughout the cell could indicate that the polypeptide achieved the desired endosome to cytosol transport, or that the polypeptide (if assembled from L-amino acids) was degraded by lysosomal enzymes and only the fluorescent tag diffused into the cytosol. Therefore, it is desirable that cytosolic entry via an endocytotic route be confirmed by a functional assay for the drug component of the polypeptide-drug product. The two examples below utilize such a functional assay.

1.) Without Endocytosis Enhancer. Hela cells used in this functional assay were stably transfected with a plasmid containing a mouse mammary tumor virus promoter (inducible with dexamethasone) controlling a gene coding for the 5' untranslated region of rabbit α-globin MRNA, followed by the coding sequence for firefly luciferase (Partridge, 1996). Cell-free and in-cell scrape-load translation studies have shown that the Morpholino antisense oligomer shown in FIG. 13 is highly effective in blocking the translation of luciferase from this gene construct. Accordingly, if the antisense oligomer of FIG. 13 gains access to the cytosolic compartment of these transfected cells, it should effect a significant reduction in luciferase activity upon dexamethasone induction, relative to untreated cells. Such a reduction in luciferase activity, measured as relative light units in a luminometer, would be indicative of successful cytosolic delivery of the Morpholino oligomer.

To test for cytosolic delivery, the polypeptide-Morpholino antisense oligonucleotide product prepared as in Example 6C was suspended in culture medium at a concentration of 5 μM. The above-described transfected Hela cells were treated with the suspension for 5 hours, and then treated for 16 hours with dexamethasone to induce luciferase synthesis. In parallel, cells in separate wells were treated with a) medium alone, b) Morpholino antisense oligo, and c) polypeptide.

Luciferase from the cells in these four wells was quantitated, and the relative light units are given in Table 3.

TABLE 3

| Treatment | Relative Light Units |
| --- | --- |
| medium alone | 100 |
| polypeptide | 105 |
| polypeptide-Morpholino product | 69 |
| Morpholino antisense oligo | 114 |

The inhibition of luciferase activity in the cells treated with the polypeptide-Morpholino product suggests that the polypeptide transported this antisense oligomer from the endosome into the cytosol of the Hela cells.

2.) With endocytosis enhancer. The experiment in the previous example was repeated with the following changes: a) the concentration of the polypeptide-Morpholino product in the medium was only 300 nM, and b) Transfectam (Promega Corp., Madison, Wis.) was added at a concentration of 20 μg/ml. It was expected that the tetra-cationic Transfectam would bind electrostatically to the polyanionic polypeptide (in its high-pH form), and the two long-chain alkane moieties of the Transfectam would serve as a lipid anchor to substantially increase the effective concentration of the complexed polypeptide-Morpholino product at the cell surface, as illustrated in FIG. 12, thereby substantially increasing the rate of entry into the cells.

Results from this experiment are given in Table 4.

TABLE 4

| Treatment | Relative Light Units |
| --- | --- |
| medium alone | 78 |
| Transfectam | 97 |
| Transfectam + polypeptide-Morpholino product | 35 |

The increased inhibition of luciferase activity in the cells treated with the combination of Transfectam and polypeptide-Morpholino product again suggests that the polypeptide transported this antisense oligo from the endosome into the cytosol of the Hela cells, and that cytosolic entry can be increased by accelerating the initial endocytosis step.

EXAMPLE 11

Enhancement of Transdermal Delivery

This example illustrates the use of a representative polypeptide composition of the invention to enhance transdermal delivery of a drug which normally exhibits very minimal passage across the epidermis. Tritiated cyclosporin A metabolite 17 is linked to a suitable polypeptide, as described in Examples 3 and 4, and the conjugate composition, with the polypeptide moiety in its low-pH form, is suspended in a suitable penetration enhancer solution which includes a lipophilic fatty acid (e.g., 10% linoleic acid/90% propylene glycol). Tritiated cyclosporin A metabolite 17, without attached polypeptide, is suspended in the same penetration enhancer solution, for comparative assessment of the rate of transdermal passage of the unmodified drug.

Each cyclosporin-containing solution is contacted with a defined area of skin on a nude hairless mouse, and small aliquots of blood are withdrawn periodically for assessment of the amount of tritiated drug which has passed through the skin and into the circulatory system.

It is claimed:

1. A composition for transporting a compound from a low-pH environment across a lipid layer to a higher-pH aqueous compartment, said composition comprising
   (a) a polypeptide containing two or more pairs of side chain carboxyl groups, where
      (i) the carboxyl groups of a pair are separated by zero, two or three amino acids,
      (ii) the polypeptide contains, at at least one terminus, an initiator sequence consisting of 5–10 amino acid residues, wherein the ratio of non-acid side chain, lipophilic residues to acid side chain residues is greater than 1, to facilitate entry of said terminus into the lipid layer,
      (iii) the sequence of the balance of the polypeptide is selected from (EXXXE)n, (XEXXE)n, and (EXEEXEXX)n, where E represents Glu or Asp, X represents a non-acid side chain amino acid, and n is an integer effective to give a total polypeptide length of up to 100 amino acid residues;
   whereby the polypeptide exhibits solubility in both hydrophilic and lipophilic environments by undergoing a reversible transition between a lipophilic form, effective to partition from said low-pH environment into the lipid layer, and a hydrophilic form, effective to partition preferentially from the lipid layer into the higher-pH aqueous compartment, and is able to traverse the lipid layer from the low-pH environment to the higher-pH compartment, and (b) the compound to be transported, covalently attached to the polypeptide.

2. The composition of claim 1, wherein each X represents an amino acid residue which is relatively non-polar and compatible with α-helix formation.

3. The composition of claim 2, wherein each X represents an amino acid residue selected from the group consisting of phenylalanine, leucine, isoleucine, norleucine, methionine, valine, alanine, norvaline, and α-amino butyric acid.

4. The composition of claim 3, wherein each X represents an amino acid residue selected from the group consisting of leucine, methionine, alanine, and α-amino butyric acid.

5. The composition of claim 1, wherein the polypeptide has a defined length of between about 10 and 50 amino acid residues.

6. The composition of claim 1, wherein the composition contains a single attached compound, attached at or near a terminus of the polypeptide.

7. The composition of claim 1, wherein the compound is selected from the group consisting of taxol, cyclosporin, and amphotericin B, and a sequence-specific nucleic acid binding polymer.

8. The composition of claim 7, wherein the compound is a sequence-specific nucleic acid binding polymer.

9. The composition of claim 1, wherein non-acid side chain residues of the polypeptide which are not used for covalent attachment of the transported compound do not contain moieties which are cationic when the polypeptide is in a low-pH α-helical conformation.

10. The composition of claim 1, wherein the polypeptide includes a group at its C-terminus or N-terminus which covalently bonds to, or includes, the terminal carboxyl or amino group, respectively, and which contains at least one remote hydroxyl or carbonyl group, which is effective to shield, by hydrogen bonding, one or more additional polar groups at or near said terminus.

11. A composition for transporting a compound from a low-pH environment across a lipid layer to a higher-pH aqueous compartment, said composition comprising (a) a polypeptide containing two or more pairs of side chain carboxyl groups, where
  (i) the carboxyl groups of a pair are separated by zero, two or three amino acids,
  (ii) the polypeptide has a length of between about 8 and about 100 amino acid residues,
  (iii) the polypeptide contains greater than 50% glutamic acid residues, and
  (iv) the polypeptide contains, at at least one terminus, an initiator polypeptide sequence consisting of 5–10 amino acid residues, wherein the ratio of non-acid side chain, lipophilic residues to acid side chain residues is greater than 1, which sequence is effective to form an alpha helix at a pH higher than the pH at which a same-length polyglutamic acid forms an alpha helix, to facilitate entry of said terminus into the lipid layer,
whereby the polypeptide exhibits solubility in both hydrophilic and lipophilic environments by undergoing a reversible transition between a lipophilic form, effective to partition from said low-pH environment into the lipid layer, and a hydrophilic form, effective to partition preferentially from the lipid layer into the higher-pH aqueous compartment, and is able to traverse the lipid layer from the low-pH environment to the higher-pH compartment, and (b) the compound to be transported, covalently attached to the polypeptide.

12. The composition of claim 11, wherein the polypeptide includes a group at its C-termiinus or N-terminus which covalently bonds to, or includes, the terminal carboxyl or amino group, respectively, and which contains at least one remote hydroxyl or carbonyl group, which is effective to shield, by hydrogen bonding, one or more additional polar groups at or near said terminus.

13. The composition of claim 12, wherein said group at the C- or N-terminus is selected from a β-alanine moiety at the C-terminus, used to initiate the synthesis of the polypeptide, a dicarboxylic acid at the N-terminus, used to terminate the polypeptide, and a combination of the two.

14. The composition of claim 11, wherein the amino acid residues in said initiator sequence are selected from the group consisting of glutamic acid, leucine, methionine, alanine, 2-aminobutyric acid, norvaline, and β-alanine, wherein the ratio of non-glutamic acid to glutamic acid residues is greater than 1.

15. A method of facilitating the transport of a compound from a low-pH environment across a lipid layer to a higher-pH aqueous compartment, comprising (a) forming a polypeptide-compound conjugate by coupling the compound covalently to a polypeptide containing two or more pairs of side chain carboxyl groups, where
  (i) the carboxyl groups of a pair are separated by zero, two or three amino acids,
  (ii) the polypeptide contains, at at least one terminus, an initiator sequence consisting of 5–10 amino acid residues, wherein the ratio of non-acid side chain, lipophilic residues to acid side chain residues is greater than 1, to facilitate entry of said terminus into the lipid layer,
  (iii) the sequence of the balance of the polypeptide is selected from (EXXXE)n, (XEXXE)n, and (EXEEXEXX)n, where E represents Glu or Asp, X represents a non-acid side chain amino acid, and n is an integer effective to give a total polypeptide length of up to 100 amino acid residues;
whereby the polypeptide exhibits solubility in both hydrophilic and lipophilic environments by undergoing a reversible transition between a lipophilic form, effective to partition from said low-pH environment into the lipid layer, and a hydrophilic form, effective to partition preferentially from the lipid layer into the higher-pH aqueous compartment; and (b) introducing the polypeptide-compound conjugate to the low-pH environment, whereby the polypeptide-compound conjugate is able to traverse the lipid layer from the low-pH environment to the higher-pH compartment.

16. The method of claim 15, wherein each X represents an amino acid residue which is relatively non-polar and compatible with α-helix formation.

17. The method of claim 16, wherein each X represents an amino acid residue selected from the group consisting of phenylalanine, leucine, isoleucine, norleucine, methionine, valine, alanine, norvaline, and α-amino butyric acid.

18. A method for facilitating the transport of a compound from a low-pH environment across a lipid layer to a higher-pH aqueous compartment, said composition comprising (a) forming a polypeptide-compound conjugate by coupling the compound covalently to a polypeptide containing two or more pairs of side chain carboxyl groups, where (i) the carboxyl groups of a pair are separated by zero, two or three amino acids,
(ii) the polypeptide has a length of between about 8 and about 100 amino acid residues,
(iii) the polypeptide contains greater than 50% glutamic acid residues, and
(iv) the polypeptide contains, at at least one terminus, an initiator polypeptide sequence consisting of 5–10 amino acid residues, wherein the ratio of non-acid side chain, lipophilic residues to acid side chain residues is greater than 1, which sequence is effective to form an alpha helix at a pH higher than the pH at which a same-length polyglutamic acid forms an alpha helix, to facilitate entry of said terminus into the lipid layer,
whereby the polypeptide exhibits solubility in both hydrophilic and lipophilic environments by undergoing a reversible transition between a lipophilic form, effective to partition from said low-pH environment into the lipid layer, and a hydrophilic form, effective to partition preferentially from the lipid layer into the higher-pH aqueous compartment, and is able to traverse the lipid layer from the low-pH environment to the higher-pH compartment; and (b) introducing the polypeptide-compound conjugate to the low-pH environment, whereby the polypeptide-compound conjugate is able to traverse the lipid layer from the low-pH environment to the higher-pH compartment.

19. The method of claim 18, wherein the polypeptide includes a group at the C-terminus or the N-terminus which covalently bonds to, or includes, the terminal carboxyl or amino group, respectively, and which contains at least one remote hydroxyl or carbonyl group, which is effective to shield, by hydrogen bonding, one or more additional polar groups at or near the polypeptide terminus.

20. The method of claim 19, wherein said group at the C- or N-terminus is selected from a β-alanine moiety at the C-terminus, used to initiate the synthesis of the polypeptide, a dicarboxylic acid at the N-terminus, used to terminate the polypeptide, and a combination of the two.

* * * * *